(12) United States Patent
Beier et al.

(10) Patent No.: US 9,000,012 B2
(45) Date of Patent: Apr. 7, 2015

(54) FUNGICIDE HYDROXIMOYL-HETEROCYCLES DERIVATIVES

(75) Inventors: Christian Beier, Bergisch Gladbach (DE); Jurgen Benting, Leichlingen (DE); David Bernier, Lyons (FR); Pierre-Yves Coqueron, Lyons (FR); Philippe Desbordes, Lyons (FR); Christophe Dubost, Charbonnieres-les-Bains (FR); Stephanie Gary, Champagne au Mont d'Or (FR); Pierre Genix, Lyons (FR); Daniela Portz, Vettweiss (DE); Ulrike Wachendorff-Neumann, Neuwied (DE)

(73) Assignee: Bayer Cropscience AG (DE)

( * ) Notice: Subject to any disclaimer, the term of this patent is extended or adjusted under 35 U.S.C. 154(b) by 0 days.

(21) Appl. No.: 13/516,675

(22) PCT Filed: Dec. 28, 2010

(86) PCT No.: PCT/EP2010/070771
§ 371 (c)(1),
(2), (4) Date: Sep. 20, 2012

(87) PCT Pub. No.: WO2011/080254
PCT Pub. Date: Jul. 7, 2011

(65) Prior Publication Data
US 2013/0040993 A1 Feb. 14, 2013

(30) Foreign Application Priority Data

Dec. 28, 2009 (EP) ..................................... 09356068

(51) Int. Cl.
| | | |
|---|---|---|
| *A01N 43/40* | (2006.01) | |
| *C07D 213/75* | (2006.01) | |
| *A01N 43/78* | (2006.01) | |
| *A01N 47/18* | (2006.01) | |
| *C07D 277/46* | (2006.01) | |
| *C07D 277/48* | (2006.01) | |
| *C07D 405/12* | (2006.01) | |
| *C07D 409/12* | (2006.01) | |
| *C07D 417/12* | (2006.01) | |

(52) U.S. Cl.
CPC .............. *C07D 213/75* (2013.01); *A01N 43/40* (2013.01); *A01N 43/78* (2013.01); *A01N 47/18* (2013.01); *C07D 277/46* (2013.01); *C07D 277/48* (2013.01); *C07D 405/12* (2013.01); *C07D 409/12* (2013.01); *C07D 417/12* (2013.01)

(58) Field of Classification Search
USPC .......................................................... 514/338
See application file for complete search history.

(56) References Cited

U.S. PATENT DOCUMENTS

| | | | | |
|---|---|---|---|---|
| 6,812,229 | B1 | 11/2004 | Ozaki et al. ................. | 514/238.8 |
| 6,939,882 | B1 | 9/2005 | Cooke et al. .................. | 514/336 |
| 7,183,299 | B2 | 2/2007 | Kobori et al. ................. | 514/361 |
| 2007/0105926 | A1 | 5/2007 | Kobori et al. ................. | 514/381 |
| 2010/0273836 | A1 | 10/2010 | Furukawa et al. ............ | 514/357 |
| 2011/0034445 | A1 | 2/2011 | Beier et al. .................. | 514/224.2 |

FOREIGN PATENT DOCUMENTS

| | | |
|---|---|---|
| EP | 1201648 A1 | 5/2002 |
| EP | 1426371 A1 | 6/2004 |
| EP | 2218711 A1 | 8/2010 |
| WO | WO 01/12604 A1 | 2/2001 |
| WO | WO 2009/075112 A1 | 6/2009 |
| WO | WO 2009/130193 A1 | 10/2009 |
| WO | WO 2011/080255 | 7/2011 |
| WO | WO 2011/080256 | 7/2011 |

OTHER PUBLICATIONS

U.S. Appl. No. 13/518,753, corresponding to PCT/EP2010/070772, having an International filed of Dec. 28, 2010, published as WO 2011/080255 by Christian Beier et al., entitled Fungicidal Hydroxiivioyl-Tetrazole Derivatives.
U.S. Appl. No. 13/519,293 corresponding to PCT/EP2010/070773, having an International filed of Dec. 28, 2010, published as WO 2011/080256 by Christian Beier et al., entitled Fungicide Hydroximoyl-Tetrazole Derivatives.
International Search Report issued Aug. 18, 2011 in corresponding International Application No. PCT/EP2010/070771, published as WO 2011/080254 A3.

*Primary Examiner* — Wu-Cheng Winston Shen
*Assistant Examiner* — Christopher R Stone
(74) *Attorney, Agent, or Firm* — Ostrolenk Faber LLP

(57) ABSTRACT

The present invention relates to hydroximoyl-heterocycle derivatives, their process of preparation, their use as fungicide active agents, particularly in the form of fungicide compositions, and methods for the control of phytopathogenic fungi, notably of plants, using these compounds or compositions.

22 Claims, No Drawings

FUNGICIDE HYDROXIMOYL-HETEROCYCLES DERIVATIVES

CROSS-REFERENCE TO RELATED APPLICATION(S)

The present application is a 35 U.S.C. §371 national phase conversion of PCT/EP2010/070771 filed Dec. 28, 2010, which claims priority of European Application No. 09356068.8 filed Dec. 28, 2009. Applicants claim priority to the foregoing patent application. The PCT International Application was published in the English language.

DESCRIPTION

The present invention relates to hydroximoyl-heterocycle derivatives, their process of preparation, their use as fungicide active agents, particularly in the form of fungicide compositions, and methods for the control of phytopathogenic fungi, notably of plants, using these compounds or compositions.

In European patent application EP1426371, there are disclosed certain tetrazoyloxime derivatives of the following chemical structure:

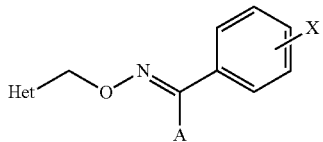

wherein A represents a tetrazolyl group, Het represents either a particular pyridinyl group or a particular thiazolyl group.

In Japanese patent application JP2004-131392, there are disclosed certain tetrazolyloxime derivatives of the following chemical structure:

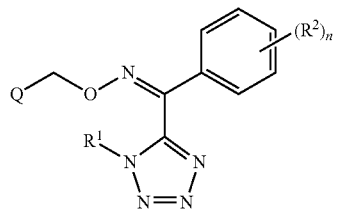

wherein Q can be selected in a list of 15 various heterocycle groups.

The compounds disclosed in these two documents do not prove to provide a comparable utility than the compounds according to the invention.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides hydroximoyl-heterocycle derivatives of formula (I)

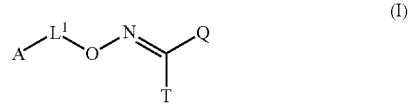

Wherein
T is selected in the list consisting of:
  a cyano group,
  a group of formula $T^a$

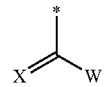

wherein
    X represents an oxygen atom, a sulfur atom, a $NR^a$ group; in which $R^a$ represents a hydrogen atom, a nitro group, a hydroxy group, a cyano group, an amino group, substituted or non-substituted $C_1$-$C_8$-alkyl, substituted or non-substituted $C_1$-$C_8$-cycloalkyl, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_2$-$C_8$-alkenyloxy, substituted or non-substituted $C_3$-$C_8$-alkynyloxy, substituted or non-substituted $C_1$-$C_8$-alkylsulfonyl, substituted or non-substituted arylsulfonyl, substituted or non-substituted benzyl, substituted or non-substituted benzyloxy, substituted or non-substituted benzylamino, substituted or non-substituted phenylamino, substituted or non-substituted aryl, or substituted or non-substituted heterocyclyl;
    W represents a hydrogen atom, a halogen atom, a hydroxy group, a cyano group, an amino group, a cyanoamino group, a sulfanyl group, hydrazino group, substituted or non-substituted N—($C_1$-$C_8$-alkyl)cyanoamino group, substituted or non-substituted $C_1$-$C_8$-alkoxyamino group, substituted or non-substituted N—($C_1$-$C_8$-alkyl)-($C_1$-$C_8$-alkoxy)-amino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-($C_1$-$C_8$)-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylsulfanyl, substituted or non-substituted $C_1$-$C_8$-alkylsulfinyl, substituted or non-substituted $C_1$-$C_8$-alkylsulfonyl, substituted or non-substituted $C_1$-$C_8$-halogenoalkylsulfanyl having 1 to 5 halogen atoms, substituted or non-substituted $C_1$-$C_8$-halogenoalkylsulfinyl having 1 to 5 halogen atoms, substituted or non-substituted $C_1$-$C_8$-halogenoalkylsulfonyl having 1 to 5 halogen atoms, substituted or non-substituted arylsulfanyl, substituted or non-substituted arylsulfinyl, substituted or non-substituted arylsulfonyl, substituted or non-substituted benzyloxy, substituted or non-substituted benzylsulfanyl, substituted or non-substituted benzylsulfinyl, substituted or non-substituted benzylsulfonyl, substituted or non-substituted benzylamino, substituted or non-substituted phenoxy, substituted or non-substituted phenylamino, substituted or non-substituted aryl, or substituted or non-substituted heterocyclyl;
a group of formula $T^b$

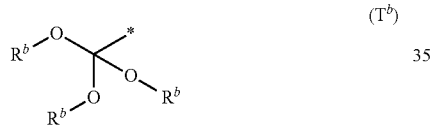

wherein
$R^b$ independently represents a substituted or non-substituted $C_1$-$C_8$-alkyl;
a group of formula $T^c$

wherein
$R^c$ independently represents a substituted or non-substituted $C_1$-$C_8$-alkyl;
an isonitrile group,
$L^1$ represents a direct bond or a divalent group consisting of —$(CR^1R^2)_n$—
wherein
n represents 1, 2, 3 or 4;
$R^1$ and $R^2$ independently represent a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, or substituted or non-substituted $C_3$-$C_8$-halogenoalkynyloxy having 1 to 5 halogen atoms.
A is selected in the list consisting of $A^2$, $A^{16}$, and $A^{18}$:

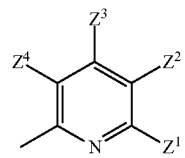  $A^2$

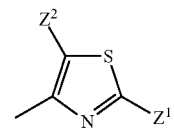  $A^{16}$

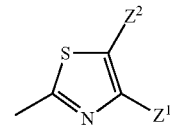  $A^{18}$ wherein
$Z^1$, $Z^2$, $Z^3$, and $Z^4$ independently represent a hydrogen atom, a halogen atom, a nitro group, a hydroxy group, a cyano group, an isonitrile group, an amino group, a cyanoamino group, a sulfanyl group, a formyl group, a substituted or non-substituted N—($C_1$-$C_8$-alkyl)cyanoamino group, a formyloxy group, a formylamino group, a carbamoyl group, a N-hydroxycarbamoyl group, a pentafluoro-$\lambda^6$-sulfanyl group, a formylamino group, substituted or non-substituted $C_1$-$C_8$-alkoxyamino group, substituted or non-substituted N—($C_1$-$C_8$-alkyl)-$C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, a substituted or non-substituted (hydroxyimino)-$C_1$-$C_6$-alkyl group, substituted or non-substituted $C_1$-$C_8$-alkyl, substituted or non-substituted tri-($C_1$-$C_8$-alkyl)silyl-$C_1$-$C_8$-alkyl, substituted or non-substituted $C_3$-$C_8$-cycloalkyl, substituted or non-substituted tri-($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted ($C_1$-$C_8$-alkoxycarbonyl)-amino, substituted or non-substituted ($C_3$-$C_8$-cycloalkoxycarbonyl)amino, substituted or non-substituted $C_1$-$C_8$-halogenoalkoxy having 1 to 5 halogen atoms, substituted or non-substituted $C_2$-$C_8$-alkenyloxy, substituted or non-substituted ($C_2$-$C_8$-alkenyloxycarbonyl)amino, substituted or non-substituted $C_2$-$C_8$-halogenoalkenyloxy having 1 to 5 halogen atoms, substituted or non-substituted $C_3$-$C_8$-alkynyloxy, substituted or non-substituted ($C_3$-$C_8$-alkynyloxycarbonyl)amino, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-($C_1$-$C_8$-alkyl)carbamoyl, substituted or non-substituted N—($C_1$-$C_8$-alkyl)hydroxycarbamoyl, substituted or non-substituted $C_1$-$C_8$-alkoxycarbamoyl, substituted or non-substituted N—($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_3$-$C_7$-cycloalkylcarbonylamino, substituted or non-substituted $C_3$-$C_7$-halogenocycloalkylcarbonylamino having 1 to 5 halogen atoms, substituted or non-substituted aryloxycarbonylamino, substituted or non-substituted heterocyclyloxycarbonylamino, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-($C_1$-$C_8$-alkyl)carbamoylamino, substituted or non-substituted di-($C_1$-$C_8$-halogenoalkyl)carbamoylamino having 1 to 5 halogen atoms, substituted or non-substituted N—($C_1$-$C_8$-alkyl)-($C_1$-$C_8$-alkylcarbamoyl)amino, substituted or non-substituted N—($C_1$-$C_8$-alkyl)-($C_1$-$C_8$-halogenoalkylcarbamoyl)amino having 1 to 5 halogen atoms, substituted or non-substituted N—($C_1$-$C_8$-alkyl)-(di-$C_1$-$C_8$-alkylcarbamoyl)amino, substituted or non-substituted N—($C_1$-$C_8$-alkyl)-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-($C_1$-$C_8$-alkyl)aminocarbonyloxy, substituted or non-substituted $C_1$-$C_8$-alkylcarbamothioyl, substituted or non-substituted di-($C_1$-$C_8$-alkyl)carbamothioyl, substituted or non-substituted N—($C_1$-$C_8$-alkyl)hydroxycarbamothioyl, substituted or non-substituted $C_1$-$C_8$-alkoxycarbamothioyl, substituted or non-substituted N—($C_1$-$C_8$-alkyl)-$C_1$-$C_8$-alkoxycarbamothioyl, substituted or non-substituted $C_1$-$C_8$-alkylthioylamino, substituted or non-substituted ($C_1$-$C_8$-alkoxythiocarbonyl)amino, substituted or non-substituted $C_1$-$C_8$-halogenoalkylthioylamino having 1 to 5 halogen atoms, substituted or non-substituted $C_1$-$C_8$-alkyl-carbamothioyloxy, substituted or non-substituted substituted or non-substituted di-($C_1$-$C_8$-alkyl)-carbamothioyloxy, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkyl-sulfonyl having 1 to 5 halogen atoms, substituted or non-substituted $C_1$-$C_8$-alkylsulfamoyl, substituted or non-substituted di-($C_1$-$C_8$-alkyl)sulfamoyl, substituted or non-substituted ($C_1$-$C_8$-alkoxyimino)-$C_1$-$C_8$-alkyl, substituted or non-substituted ($C_2$-$C_8$-alkenyloxyimino)-$C_1$-$C_8$-alkyl, substituted or non-substituted ($C_2$-$C_8$-alkynyloxyimino)-$C_1$-$C_8$-alkyl, substituted or non-substituted (benzyloxyimino)-$C_1$-$C_8$-alkyl, substituted or non-substituted benzyloxy, substituted or non-substituted benzylsulfanyl, substituted or non-substituted benzylamino, substituted or non-substituted phenoxy, substituted or non-substituted phenylsulfanyl, substituted or non-substituted phenylamino, substituted or non-substituted aryl, substituted or non-substituted arylcarbonylamino, substituted or non-substituted heterocyclylcarbonylamino, substituted or non-substituted aryl-$C_1$-$C_8$-alkyl, substituted or non-substituted tri-($C_1$-$C_8$-alkyl)-silyloxy, substituted or non-substituted $C_1$-$C_8$-alkylsulfanylamino, substituted or non-substituted $C_1$-$C_8$-halogenoalkyl-sulfanylamino having 1 to 5 halogen atoms, substituted or non-substituted $C_1$-$C_8$-alkylsulfinylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri-($C_1$-$C_8$-alkyl)-silyl, substituted or non-substituted ($C_1$-$C_8$-alkylideneamino)oxy, substituted or non-substituted ($C_3$-$C_8$-alkenylideneamino)oxy, substituted or non-substituted ($C_3$-$C_8$-alkynylideneamino)oxy, substituted or non-substituted (benzylideneamino)oxy, substituted or non-substituted aryl-cyclopropylcarbonylamino, substituted or non-substituted $C_3$-$C_8$-cycloalkenylcarbonylamino, substituted or non-substituted $C_2$-$C_8$-alkenylcarbonylamino, substituted or non-substituted $C_2$-$C_8$-alkynylcarbonylamino, substituted or non-substituted $C_5$-$C_{12}$-fused bicycloalkylcarbonylamino, or substituted or non-substituted $C_5$-$C_{12}$-fused bicycloalkenylcarbonylamino;

Q is selected in the list consisting of $Q^1$:

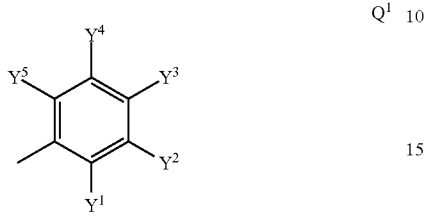

wherein $Y^1$ to $Y^5$ independently represent a hydrogen atom, a nitro group, a hydroxy group, a cyano group, an isonitrile group, an amino group, a sulfanyl group, a formyl group, a formyloxy group, a formylamino group, a carbamoyl group, a N-hydroxycarbamoyl group, a pentafluoro-$\lambda^6$-sulfanyl group, a formylamino group, substituted or non-substituted $C_1$-$C_8$-alkoxyamino group, substituted or non-substituted N—($C_1$-$C_8$-alkyl)-$C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, substituted or non-substituted (hydroxyimino)-$C_1$-$C_6$-alkyl group, substituted or non-substituted $C_1$-$C_8$-alkyl, substituted or non-substituted tri-($C_1$-$C_8$-alkyl)silyl-$C_1$-$C_8$-alkyl, substituted or non-substituted $C_3$-$C_7$-cycloalkyl, substituted or non-substituted tri-($C_1$-$C_8$-alkyl)silyl-$C_3$-$C_7$-cycloalkyl, substituted or non-substituted $C_1$-$C_8$-halogenoalkyl having 1 to 5 halogen atoms, substituted or non-substituted $C_3$-$C_7$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-($C_1$-$C_8$-alkyl)carbamoyl, substituted or non-substituted N—($C_1$-$C_8$-alkyl)hydroxycarbamoyl, substituted or non-substituted $C_1$-$C_8$-alkoxycarbamoyl, substituted or non-substituted N—($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-($C_1$-$C_8$-alkyl)carbamoylamino, substituted or non-substituted di-($C_1$-$C_8$-halogenoalkyl)carbamoylamino having 1 to 5 halogen atoms, substituted or non-substituted N—($C_1$-$C_8$-alkyl)-($C_1$-$C_8$-alkylcarbamoyl)amino, substituted or non-substituted N—($C_1$-$C_8$-alkyl)-($C_1$-$C_8$-halogenoalkylcarbamoyl)amino having 1 to 5 halogen atoms, substituted or non-substituted N—($C_1$-$C_8$-alkyl)-[di-($C_1$-$C_8$-alkyl)carbamoyl]amino, substituted or non-substituted N—($C_1$-$C_8$-alkyl)-[di-($C_1$-$C_8$-halogenoalkyl)carbamoyl]amino having 1 to 5 halogen atoms, substituted or non-substituted $C_1$-$C_8$-alkylaminocarbonyloxy, substituted or non-substituted di-($C_1$-$C_8$-alkylamino)carbonyloxy, substituted or non-substituted $C_1$-$C_8$-alkylcarbamothioyl, substituted or non-substituted di-($C_1$-$C_8$-alkyl)carbamothioyl, substituted or non-substituted N—($C_1$-$C_8$-alkyl)hydroxycarbamothioyl, substituted or non-substituted $C_1$-$C_8$-alkoxycarbamothioyl, substituted or non-substituted N—($C_1$-$C_8$-alkyl)-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted $C_1$-$C_8$-alkyl-carbamothioyloxy, substituted or non-substituted substituted or non-substituted di-($C_1$-$C_8$-alkyl)-carbamothioyloxy, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylsulfamoyl, substituted or non-substituted di-($C_1$-$C_8$-alkyl)sulfamoyl, substituted or non-substituted ($C_1$-$C_8$-alkoxyimino)-$C_1$-$C_8$-alkyl, substituted or non-substituted ($C_2$-$C_8$-alkenyloxyimino)-$C_1$-$C_8$-alkyl, substituted or non-substituted ($C_3$-$C_8$-alkynyloxyimino)-$C_1$-$C_8$-alkyl, substituted or non-substituted (benzyloxyimino)-$C_1$-$C_8$-alkyl, substituted or non-substituted benzyloxy, substituted or non-substituted benzylsulfanyl, substituted or non-substituted benzylamino, substituted or non-substituted phenoxy, substituted or non-substituted phenylsulfanyl, substituted or non-substituted phenylamino, substituted or non-substituted aryl, substituted or non-substituted aryl-$C_1$-$C_8$-alkyl, substituted or non-substituted tri-($C_1$-$C_8$-alkyl)-silyloxy, substituted or non-substituted $C_1$-$C_8$-alkylsulfanylamino, substituted or non-substituted $C_1$-$C_8$-halogenoalkylsulfanylamino having 1 to 5 halogen atoms, substituted or non-substituted $C_1$-$C_8$-alkylsulfinylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri-($C_1$-$C_8$-alkyl)-silyl, substituted or non-substituted ($C_1$-$C_8$-alkylideneamino)oxy, substituted or non-substituted ($C_1$-$C_8$-alkenylideneamino)oxy, substituted or non-substituted ($C_1$-$C_8$-alkynylideneamino)oxy, or substituted or non-substituted (benzylideneamino)oxy;

as well as salts, N-oxides, metallic complexes and metalloidic complexes thereof or (E) and (Z) isomers and mixtures thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the heterocyclyloxime derivative of formula (I) includes (E) or (Z) isomer, and these stereoisomers form part of the present invention.

According to the invention, the following generic terms are generally used with the following meanings:

halogen means fluorine, chlorine, bromine or iodine;

heteroatom can be nitrogen, oxygen or sulfur;

unless indicated otherwise, a group or a substituent that is substituted according to the invention can be substituted by one or more of the following groups or atoms: a halogen atom, a nitro group, a hydroxy group, a cyano group, an isonitrile group, an amino group, a sulfanyl group, a pentafluoro-$\lambda^6$-sulfanyl group, a formyl group, a formyloxy group, a formylamino group, a carbamoyl group, a N-hydroxycarbamoyl group, a formylamino group, a (hydroxyimino)-$C_1$-$C_8$-alkyl group, a $C_1$-$C_8$-alkyl, a $C_1$-$C_8$-halogenoalkyl having 1 to 5 halogen atoms, a tri-($C_1$-$C_8$-alkyl)silyl-$C_1$-$C_8$-alkyl, $C_3$-$C_7$-cycloalkyl, tri-($C_1$-$C_8$-alkyl)silyl-$C_3$-$C_7$-cycloalkyl, a $C_3$-$C_7$-halogenocycloalkyl having 1 to 5 halogen atoms, $C_3$-$C_7$-cycloalkoxy, a $C_3$-$C_7$-halogenocycloalkoxy having 1 to 5 halogen atoms, $C_3$-$C_7$-cycloalkyl-$C_1$-$C_8$-alkoxy, a $C_3$-$C_7$-halogenocycloalkyl-$C_1$-$C_8$-alkoxy having 1 to 5 halogen atoms, a $C_2$-$C_8$-alkenyl, a $C_2$-$C_8$-alkynyl, a $C_2$-$C_8$-alkenyloxy, a $C_3$-$C_8$-alkynyloxy, a $C_1$-$C_8$-alkylamino, a di-($C_1$-$C_8$-alkyl)amino, a $C_1$-$C_8$-alkoxy, a $C_1$-$C_8$-halogenoalkoxy having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-($C_1$-$C_8$-alkyl)carbamoyl, a N—($C_1$-$C_8$-alkyl)hydroxycarbamoyl, a $C_1$-$C_8$-alkoxycarbamoyl, a N—($C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, a $C_1$-$C_8$-alkylaminocarbonyloxy, a di-($C_1$-$C_8$-alkyl)aminocarbonyloxy, a $C_1$-$C_8$-alkyloxycarbonyloxy, a $C_1$-$C_8$-alkylsulfanyl, a $C_1$-$C_8$-halogenoalkylsulfanyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_8$-alkylsulfamoyl, a di-($C_1$-$C_8$-alkyl)sulfamoyl, a ($C_1$-$C_8$-alkoxyimino)-$C_1$-$C_8$-alkyl, a ($C_2$-$C_6$-alkenyloxyimino)-$C_1$-$C_8$-alkyl, a ($C_3$-$C_6$-alkynyloxyimino)-$C_1$-$C_8$-alkyl, (benzyloxyimino)-$C_1$-$C_8$-alkyl, $C_1$-$C_8$-alkoxyalkyl, $C_1$-$C_8$-halogenoalkoxyalkyl having 1 to 5 halogen atoms, benzyloxy, benzylsulfanyl, benzylamino, phenoxy, phenylsulfanyl, or phenylamino;

the term "aryl" means phenyl or naphthyl;

the term "heterocyclyl" means saturated or unsaturated, monocyclic or fused bicyclic 4-, 5-, 6-, 7-, 8-, 9-, or 10-membered ring comprising up to 4 heteroatoms selected in the list consisting of N, O, S;

in the case of an amino group or the amino moiety of any other amino-comprising group, substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino group or piperidinyl group.

Preferred compounds of formula (I) according to the invention are those wherein T represents a cyano group or a group of formula $T^a$.

Preferred compounds of formula (I) according to the invention are those wherein X represents an oxygen atom.

Other preferred compounds of formula (I) according to the invention are those wherein $R^a$ represents a hydrogen atom, a hydroxy group, substituted or non-substituted $C_1$-$C_8$-alkyl, substituted or non-substituted $C_3$-$C_7$-cycloalkyl.

Other preferred compounds of formula (I) according to the invention are those wherein $R^a$ independently represents a hydrogen atom, a methyl group or an ethyl group.

Other preferred compounds of formula (I) according to the invention are those wherein W represents a hydrogen atom, a halogen atom, a hydroxy group, a cyano group, an amino group, a cyanoamino group, a sulfanyl group, a hydrazino group, a substituted or non-substituted N—($C_1$-$C_8$-alkyl)cyanoamino group, substituted or non-substituted $C_1$-$C_8$-alkoxyamino group, substituted or non-substituted N—($C_1$-$C_8$-alkyl)-$C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, substituted or non-substituted $C_1$-$C_8$-alkyl, substituted or non-substituted $C_1$-$C_7$-cycloalkyl, substituted or non-substituted $C_1$-$C_8$-halogenoalkyl having 1 to 5 halogen atoms, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_1$-$C_8$-alkylsulfanyl.

Other more preferred compounds of formula (I) according to the invention are those wherein W represents a hydroxy group, an amino group, a hydrazino group, substituted or non-substituted $C_1$-$C_8$-alkoxyamino group, substituted or non-substituted N—($C_1$-$C_8$-alkyl)-$C_1$-$C_8$-alkoxyamino group, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_1$-$C_8$-alkylsulfanyl.

Other even more preferred compounds of formula (I) according to the invention are those wherein W represents a hydroxy group, an amino group, a hydrazino group, methylamino, ethylamino, dimethylamino, ethylmethylamino or methoxy;

Other preferred compounds of formula (I) according to the invention are those wherein $R^b$ represents methyl or ethyl.

Other preferred compounds of formula (I) according to the invention are those wherein $R^c$ represents methyl or ethyl.

Other preferred compounds of formula (I) according to the invention are those wherein $L^1$ represents a direct bond or a divalent group consisting of —$(CR^1R^2)_n$— wherein n represents 1 or 2;

$R^1$ and $R^2$ independently represent a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms.

Other more preferred compounds of formula (I) according to the invention are those wherein $L^1$ represents a direct bond or a divalent group consisting of —$(CR^1R^2)$—, wherein $R^1$ and $R^2$ are independently selected in the list consisting of hydrogen, halogen, methyl, ethyl, isopropyl, trifluoromethyl, difluoromethyl, allyl, ethynyl, propargyl, cyclopropyl, methoxy, trifluoromethoxy and cyano.

Other preferred compounds of formula (I) according to the invention are those wherein $Z^1$ represents independently represent a hydrogen atom, a halogen atom, a nitro group, a hydroxy group, a cyano group, an amino group, a formylamino group, substituted or non-substituted $C_1$-$C_8$-alkyl, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted ($C_1$-$C_8$-alkoxycarbonyl)amino, substituted or non-substituted ($C_3$-$C_8$-cycloalkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted $C_1$-$C_8$-alkylcarbamoyl, substituted or non-substituted di-($C_1$-$C_8$-alkyl)carbamoyl, substituted or non-substituted N—($C_1$-$C_8$-alkyl)hydroxycarbamoyl, substituted or non-substituted $C_1$-$C_8$-alkoxycarbamoyl, substituted or non-substituted N—($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-alkylcarbonylamino, substituted or non-substituted aryloxycarbonylamino, substituted or non-substituted heterocyclyloxycarbonylamino, substituted or non-substituted $C_1$-$C_8$-alkylcarbamoylamino, substituted or non-substituted $C_1$-$C_8$-alkylthioylamino, substituted or non-substituted ($C_1$-$C_8$-alkoxythiocarbonyl)amino, substituted or non-substituted (arylcarbonyl)amino, substituted or non-substituted (heterocyclylcarbonyl)-amino, substituted or non-substituted arylcyclopropylcarbonylamino, substituted or non-substituted $C_3$-$C_7$-cycloalkenylcarbonylamino, substituted or non-substituted $C_2$-$C_8$-alkenylcarbonylamino, substituted or non-substituted $C_2$-$C_8$-alkynylcarbonylamino, substituted or non-substituted $C_8$-$C_{12}$-fused bicycloalkylcarbonylamino, substituted or non-substituted $C_5$-$C_{12}$-fused bicycloalkenylcarbonylamino.

Other more preferred compounds of formula (I) according to the invention are those wherein $Z^1$ represents an amino group, a formylamino group, substituted or non-substituted ($C_1$-$C_8$-alkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted $C_1$-$C_8$-alkylthioylamino, substituted or non-substituted (arylcarbonyl)amino, substituted or non-substituted (heterocyclylcarbonyl)amino, substituted or non-substituted aryl-cyclopropylcarbonylamino, substituted or non-substituted $C_3$-$C_7$-cycloalkenylcarbonylamino, substituted or non-substituted $C_2$-$C_8$-alkenylcarbonylamino, substituted or non-substituted $C_2$-$C_8$-alkynylcarbonylamino.

Other even more preferred compounds of formula (I) according to the invention are those wherein $Z^1$ represents an amino group, a formylamino group, substituted or non-substituted ($C_4$-$C_8$-alkoxycarbonyl)amino, substituted or non-substituted ($C_4$-$C_8$-alkenyloxycarbonyl)amino, substituted or non-substituted ($C_4$-$C_8$-alkynyloxycarbonyl)amino, substituted or non-substituted $C_4$-$C_8$-alkylthioylamino, substituted or non-substituted (arylcarbonyl)amino, substituted or non-substituted (heterocyclylcarbonyl)amino.

Other preferred compounds of formula (I) according to the invention are those wherein $Z^2$ to $Z^4$ independently represent a hydrogen atom, a halogen atom, a cyano group, substituted or non-substituted $C_1$-$C_8$-alkyl, substituted or non-substituted $C_3$-$C_7$-cycloalkyl, substituted or non-substituted $C_1$-$C_8$-halogenoalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted phenoxy, substituted or non-substituted aryl, substituted or non-substituted aryl-$C_1$-$C_8$-alkyl.

Other more preferred compounds of formula (I) according to the invention are those wherein $Z^2$ to $Z^4$ are independently selected in the list consisting of hydrogen, halogen, methyl, ethyl, isopropyl, isobutyl, terbutyl, trifluoromethyl, difluoromethyl, allyl, ethynyl, propargyl, cyclopropyl, methoxy, trifluoromethoxy, acetyl, and cyano.

Other preferred compounds of formula (I) according to the invention are those wherein $Y^1$ to $Y^5$ independently represent a hydrogen atom, a halogen atom, a cyano group, an amino group, a sulfanyl group, a pentafluoro-$\lambda^6$-sulfanyl group, substituted or non-substituted $C_1$-$C_8$-alkyl, substituted or non-substituted tri-($C_1$-$C_8$-alkyl)silyl-$C_1$-$C_8$-alkyl, substituted or non-substituted $C_3$-$C_7$-cycloalkyl, substituted or non-substituted tri-($C_1$-$C_8$-alkyl)silyl-$C_3$-$C_7$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-($C_1$-$C_8$-alkyl)carbamoyl, substituted or non-substituted N—($C_1$-$C_8$-alkyl)hydroxycarbamoyl, substituted or non-substituted $C_1$-$C_8$-alkoxycarbamoyl, substituted or non-substituted N—($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-($C_1$-$C_8$-alkyl)carbamothioyl, substituted or non-substituted N—($C_1$-$C_8$-alkyl)hydroxycarbamothioyll, substituted or non-substituted $C_1$-$C_8$-alkoxycarbamothioyl, substituted or non-substituted N—($C_1$-$C_8$-alkyl)-$C_1$-$C_8$-alkoxycarbamothioyl, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted ($C_1$-$C_8$-alkoxyimino)-$C_1$-$C_8$-alkyl, substituted or non-substituted ($C_2$-$C_8$-alkenyloxyimino)-$C_1$-$C_8$-alkyl, substituted or non-substituted ($C_3$-$C_8$-alkynyloxyimino)-$C_1$-$C_8$-alkyl, substituted or non-substituted (benzyloxyimino)-$C_1$-$C_8$-alkyl, substituted or non-substituted benzyloxy, substituted or non-substituted benzylsulfanyl, substituted or non-substituted phenoxy, substituted or non-substituted phenylsulfanyl, substituted or non-substituted aryl, substituted or non-substituted aryl-$C_1$-$C_8$-alkyl, substituted or non-substituted tri-($C_1$-$C_8$-alkyl)-silyloxy, substituted or non-substituted tri-($C_1$-$C_8$-alkyl)-silyl.

Other more preferred compounds of formula (I) according to the invention are those wherein $Y^1$ to $Y^5$ independently represent a hydrogen atom, a halogen atom, methyl, isopropyl, isobutyl, tertbutyl, trifluoromethyl, difluoromethyl, allyl, ethynyl, propargyl, cyclopropyl, methoxy, trifluoromethoxy and cyano.

The above mentioned preferences with regard to the substituents of the compounds of formula (I) according to the invention can be combined in various manners. These combinations of to preferred features thus provide sub-classes of compounds according to the invention. Examples of such sub-classes of preferred compounds according to the invention can combine:

preferred features of A with preferred features of one or more of $L^1$, T, X and Q;
preferred features of X with preferred features of one or more of $L^1$, T, A and Q;
preferred features of $L^1$ with preferred features of one or more of A, T, X and Q;
preferred features T with preferred features of one or more of A, $L^1$, X and Q;
preferred features of Q with preferred features of one or more of A, $L^1$, X and T.

In these combinations of preferred features of the substituents of the compounds according to the invention, the said preferred features can also be selected among the more preferred features of each of A, X, $L^1$, T and Q; so as to form most preferred subclasses of compounds according to the invention.

The preferred features of the other substituents of the compounds according to the invention can also be part of such sub-classes of preferred compounds according to the invention, notably the groups of substituents $T^a$, $T^b$, $T^b$, X, W, $R^a$, $R^b$, $R^c$, n, $R^1$, $R^2$, $Z^1$ to $Z^4$, and $Y^1$ to $Y^5$.

The present invention also relates to a process for the preparation of compounds of formula (I), Thus, according to a further aspect of the present invention, there is a provided a process P1 for the preparation of compounds of formula (I), as herein-defined, as illustrated by the following reaction scheme:

Process P1

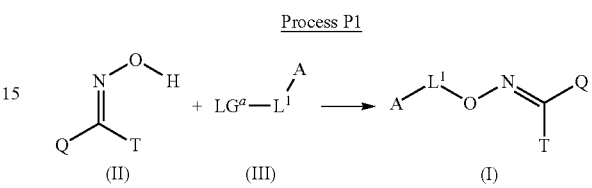

wherein T, A, Q and $L^1$ are as herein-defined and $LG^a$ represents a leaving group. Suitable leaving groups can be selected in the list consisting of a halogen atom or other customary nucleofugal groups such as triflate, mesylate, or tosylate.

For the compounds of formula (Ia) according to the invention when $Z^1$, $Z^2$, $Z^3$, or $Z^4$ represents a hydroxyl group, a sulfanyl group, an amino group, substituted or non-substituted $C_1$-$C_8$-alkylamino, substituted or non-substituted $C_1$-$C_8$-halogenoalkylamino having 1 to 5 halogen atoms, a formylamino group, substituted or non-substituted $C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-($C_1$-$C_8$-alkyl)carbamoylamino, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkylcarbamothioyl)-amino, substituted or non-substituted [di-($C_1$-$C_8$-alkyl)-carbamothioyl]-amino, process P1 according to the invention can be completed by a further step comprising the additional modification of this group, notably by a reaction of alkylation, acylation, alkoxycarbonylation, alkylaminocarbonylation and alkylaminothiocarbonylation, to yield to a compound of formula (Ib), according to known methods. In such a case there is provided a process P2 according to the invention and such a process P2 can be illustrated by the following reaction schemes:

Process P2

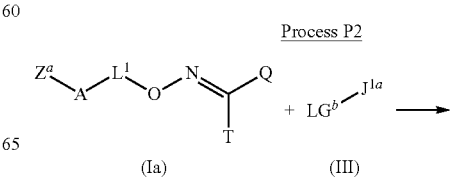

-continued

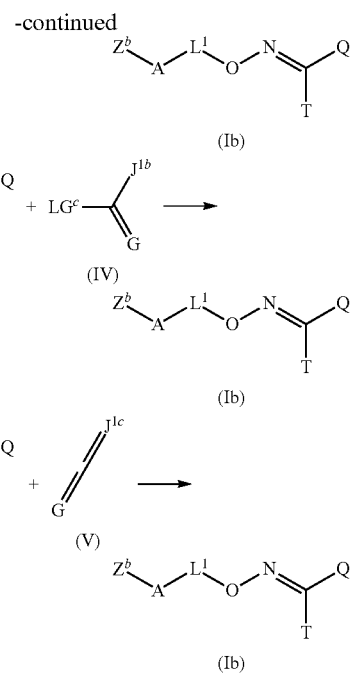

wherein

T, A, Q and $L^1$ are as herein-defined, $LG^b$ and $LG^c$ represent a leaving group, $J^{1a}$ optionally represents substituted or non-substituted $C_1$-$C_8$-alkyl, substituted or non-substituted $C_1$-$C_8$-halogenoalkyl having 1 to 5 halogen atoms, $J^{1b}$ optionally represents a hydrogen atom, substituted or non-substituted $C_1$-$C_8$-alkyl, substituted or non-substituted $C_1$-$C_8$-halogenoalkyl having 1 to 5 halogen atoms, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_1$-$C_8$-halogenoalkoxy having 1 to 5 halogen atoms, $J^{1c}$ optionally represents substituted or non-substituted $C_1$-$C_8$-alkylamino;

$Z^a$ represents a hydroxyl group, a sulfanyl group, an amino group, substituted or non-substituted $C_1$-$C_8$-alkylamino, substituted or non-substituted $C_1$-$C_8$-halogenoalkylamino having 1 to 5 halogen atoms, a formylamino group, substituted or non-substituted $C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-($C_1$-$C_8$-alkyl)carbamoylamino, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-amino, substituted or non-substituted [di-($C_1$-$C_8$-alkyl)-carbamothioyl]-amino, G represents an oxygen atom or a sulfur atom;

$Z^b$ represents a formyloxy group, a formylamino group, a formylamino group, substituted or non-substituted N—($C_1$-$C_8$-alkyl)-$C_1$-$C_8$-alkoxyamino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-($C_1$-$C_8$-alkyl)carbamoylamino, substituted or non-substituted di-($C_1$-$C_8$-halogenoalkyl)carbamoylamino having 1 to 5 halogen atoms, substituted or non-substituted N—($C_1$-$C_8$-alkyl)-($C_1$-$C_8$-alkylcarbamoyl)amino, substituted or non-substituted N—($C_1$-$C_8$-alkyl)-($C_1$-$C_8$-halogenoalkylcarbamoyl)amino having 1 to 5 halogen atoms, substituted or non-substituted N—($C_1$-$C_8$-alkyl)-di-($C_1$-$C_8$-alkyl)carbamoylamino, substituted or non-substituted N—($C_1$-$C_8$-alkyl)-di-($C_1$-$C_8$-halogenoalkyl)carbamoylamino having 1 to 5 halogen atoms, substituted or non-substituted $C_1$-$C_8$-alkylaminocarbonyloxy, substituted or non-substituted di-($C_1$-$C_8$-alkyl)aminocarbonyloxy, substituted or non-substituted $C_1$-$C_8$-alkylcarbamothioyl, substituted or non-substituted di-($C_1$-$C_8$-alkyl)carbamothioyl, substituted or non-substituted N—($C_1$-$C_8$-alkyl)hydroxycarbamothioyl, substituted or non-substituted $C_1$-$C_8$-alkoxycarbamothioyl, substituted or non-substituted N—($C_1$-$C_8$-alkyl)-$C_1$-$C_8$-alkoxycarbamothioyl, substituted or non-substituted ($C_1$-$C_8$-alkyl-carbamothioyl)-amino, substituted or non-substituted substituted or non-substituted [di-($C_1$-$C_8$-alkyl)-carbamothioyl]-amino, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted benzyloxy, substituted or non-substituted benzylsulfanyl, substituted or non-substituted benzylamino, substituted or non-substituted tri-($C_1$-$C_8$-alkyl)-silyloxy.

Suitable leaving groups can be selected in the list consisting of a halogen atom or other customary nucleofugal groups such as alkoxy, alkylsulfanyl, hydroxide, cyanide, triflate, mesylate, or tosylate.

If $Z^1$, $Z^2$, $Z^3$, or $Z^4$ represent a protected amino group, carrying out process P2 would previously require a deprotection step in order to yield the amino group. Amino-protecting groups and related methods of cleavage thereof are well known from the skilled man.

According to the invention, processes P1 and P2 may be performed if appropriate in the presence of a solvent and if appropriate in the presence of a base.

According to the invention, processes P1 and P2 may be performed if appropriate in the presence of a catalyst. Suitable catalyst may be chosen as being 4-(dimethylamino)pyridine, 1-hydroxybenzotriazole or dimethylformamide.

In case LG$^c$ represents a hydroxy group, the process P2 according to the present invention may be performed in the presence of condensing agent. Suitable condensing agent may be chosen as being acid halide former, such as phosgene, phosphorous tri-bromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]-triazin-2-yl)-4-methylmorpholinium chloride hydrate or bromo-tripyrrolidino-phosphonium-hexafluorophosphate.

Suitable solvents for carrying out processes P1 and P2 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, trichlorotoluene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide, or sulfones, such as sulfolane.

Suitable bases for carrying out processes P1 and P2 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-(dimethylamino)pyridine, 1,4-diazabicyclo[2.2.2]octane (DABCO), 1,5-diazabicyclo[4.3.0]non-5-ene (DBN) or 1,8-diaza-bicyclo[5.4.0]undec-7-ene (DBU).

When carrying out processes P1 and P2 according to the invention, the reaction temperature can independently be varied within a relatively wide range. Generally, process P1 according to the invention is carried out at temperatures between −80° C. and 160° C. A way to control the temperature for the processes P1 and P2 according to the invention is to use micro-wave technology.

Processes P1 and P2 according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that may still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

Compounds of formula (II), useful as a starting material, can be prepared, for example, by to reacting hydroxylamine with the corresponding ketone according to the method described by F. Heaney et al. (*Organic and Biomolecular Chemistry* 2003, 7, 1122) or by reacting an alkyl nitrite with the corresponding benzylic methylene according to the method described by Y. Kondo et al. (*Bioscience, Biotechnology, and Biochemistry* 2007, 71, 2781).

In a further aspect, the present invention relates to compounds of formula (IIa) useful as intermediate compounds or materials for the process of preparation according to the invention. The present invention thus provides compounds of formula (IIa):

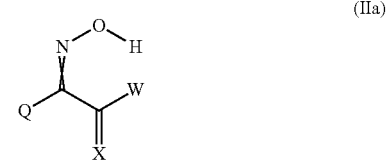

(IIa)

wherein Q is a substituted or non-substituted phenyl group, X represents an oxygen atom or a sulfur atom and W is a non-substituted amino group or an amino group that can be substituted by one or two, similar or different, $C_1$-$C_8$-alkyl group, $C_3$-$C_7$-cycloalkyl group, cyano, amino, $C_1$-$C_8$-alkylamino group, di-($C_1$-$C_8$-alkyl)amino group, hydroxy, $C_1$-$C_8$-alkoxy group or $C_3$-$C_7$-cycloalkoxy group, with the exclusion of:
2-(2-chlorophenyl)-2-(hydroxyimino)-N-methylacetamide,
2-(hydroxyimino)-2-(2-hydroxyphenyl)-N-methylacetamide,
2-(hydroxyimino)-2-(2-iodophenyl)-N,N-dimethylacetamide,
2-(hydroxyimino)-2-(4-methoxyphenyl)-N-methylacetamide,
2-(hydroxyimino)-2-[2-(hydroxymethyl)phenyl]-N-methylacetamide,
2-(hydroxyimino)-2-phenyl-N-propylacetamide,
2-(hydroxyimino)-N,N-dimethyl-2-(2-phenoxyphenyl)acetamide,
2-(hydroxyimino)-N,N-dimethyl-2-phenylacetamide,
2-(hydroxyimino)-N-isopropyl-2-(4-methoxyphenyl)acetamide,
2-(hydroxyimino)-N-isopropyl-2-phenylacetamide,
2-(hydroxyimino)-N-methyl-2-(2-methylphenyl)acetamide,
2-(hydroxyimino)-N-methyl-2-(2-phenoxyphenyl)acetamide, 2-(hydroxyimino)-N-methyl-2-(4-methylphenyl)acetamide,
2-(hydroxyimino)-N-methyl-2-[2-(4-methylphenoxy)phenyl]acetamide,
2-(hydroxyimino)-N-methyl-2-phenylacetamide,
N,N-diethyl-2-(hydroxyimino)-2-phenylacetamide,
N-allyl-2-(hydroxyimino)-2-phenylacetamide,
N-allyl-2-(hydroxyimino)-N-methyl-2-phenylacetamide,
N-butyl-2-(hydroxyimino)-2-phenylacetamide,
N-ethyl-2-(hydroxyimino)-2-phenylacetamide,
N-heptyl-2-(hydroxyimino)-2-phenylacetamide,
N-tert-butyl-2-(hydroxyimino)-2-phenylacetamide,
1-(azepan-1-yl)-2-(hydroxyimino)-2-phenylethanone,
2-(hydroxyimino)-2-phenyl-1-(3-phenylpyrrolidin-1-yl) ethanone,
2-(hydroxyimino)-1-(morpholin-4-yl)-2-phenylethanone,
2-(hydroxyimino)-2-phenyl-1-(piperidin-1-yl)ethanone,
methyl 1-(2-(hydroxyimino)-2-phenylacetyl)-L-prolinate,
N-cyclohexyl-2-(hydroxyimino)-2-phenylacetamide,
2-(hydroxyimino)-N-(morpholin-4-yl)-2-phenylacetamide,
2-(hydroxyimino)-2-phenylacetohydrazide,
2-(4-chlorophenyl)-2-(hydroxyimino)ethanethioamide,
2-(2,6-dichlorophenyl)-2-(hydroxyimino)ethanethioamide,
N-hydroxy-2-(hydroxyimino)-2-(4-methylphenyl)acetamide,
N-hydroxy-2-(hydroxyimino)-2-phenylacetamide,
2-(2-acetamidophenyl)-N-hydroxy-2-(hydroxyimino)acetamide.

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyols and derivatives of the above compounds containing sulfate, sulfonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible to flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous. The composition according to the invention comprising a mixture of a compound of formula (I) with a bactericide compound can also be particularly advantageous.

Examples of suitable fungicide mixing partners can be selected in the following lists:
(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1 RS,4SR,9RS and anti-epimeric racemate 1 RS,4SR,9SR) (881685-58-1), (2.12) isopyrazam (anti-epimeric racemate 1 RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570) and salts thereof.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) dimoxystrobin (141600-52-4), (3.6) enestroburin (238410-11-2) (WO 2004/058723), (3.7) famoxadone (131807-57-3) (WO 2004/058723), (3.8) fenamidone (161326-34-7) (WO 2004/058723), (3.9) fluoxastrobin (361377-29-9) (WO 2004/058723), (3.10) to kresoxim-methyl (143390-89-0) (WO 2004/058723), (3.11) metominostrobin (133408-50-1) (WO 2004/058723), (3.12) orysastrobin (189892-69-1) (WO 2004/058723), (3.13) picoxystrobin (117428-22-5) (WO 2004/058723), (3.14) pyraclostrobin (175013-18-0) (WO 2004/058723), (3.15) pyrametostrobin (915410-70-7) (WO 2004/058723), (3.16) pyraoxystrobin (862588-11-2) (WO 2004/058723), (3.17) pyribencarb (799247-52-2) (WO 2004/058723), (3.18) trifloxystrobin (141517-21-7) (WO 2004/058723), (3.19) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.20) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723) and salts thereof, (3.21) (2E)-2-(methoxyimino)-N-methyl-2-{2-[(E)-({1-[3-(trifluoromethyl)phenyl]ethoxy}imino)methyl]phenyl}ethanamide (158169-73-4), (3.22) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.23) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.24) 2-chloro-N-(1,1,3-trimethyl-2,3-dihydro-1H-inden-4-yl)pyridine-3-carboxamide (119899-14-8), (3.25) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.26) methyl (2E)-2-{2-[({cyclopropyl[(4-methoxyphenyl)imino]methyl}sulfanyl)methyl]phenyl}-3-methoxyprop-2-enoate (149601-03-6), (3.27) N-(3-ethyl-3,5,5-trimethylcyclohexyl)-3-(formylamino)-2-hydroxybenzamide (226551-21-9), (3.28) 2-{2-[(2,5-dimethylphenoxy)methyl]phenyl}-2-methoxy-N-methylacetamide (173662-97-0), (3.29) (2R)-2-{2-[(2,5-dimethylphenoxy)methyl]phenyl}-2-methoxy-N-methylacetamide (394657-24-0) and salts thereof.

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3), (4.14) 3-chloro-5-(6-chloropyridin-3-yl)-6-methyl-4-(2,4,6-trifluorophenyl)pyridazine (1002756-87-7) and salts thereof.

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulfur and sulfur preparations including calcium polysulfide (7704-34-9), (5.31) thiram (137-26-8), (5.32) tolylfluanid (731-27-1), (5.33) zineb (12122-67-7), (5.34) ziram (137-30-4) and salts thereof.

(6) Compounds capable to induce a host defence, like for example (6.1) acibenzolar-5-methyl (135158-54-2), (6.2) isotianil (224049-04-1), (6.3) probenazole (27605-76-1), (6.4) tiadinil (223580-51-6) and salts thereof.

(7) Inhibitors of the amino acid and/or protein biosynthesis, for example, (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and salts thereof.

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1) and (11.6) tricyclazole (41814-78-2).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, like for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) chlazafenone (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulfate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrrolnitrine (1018-71-9) (EP-A 1 559 320), (15.46) tebufloquin (376645-78-2), (15.47) tecloftalam (76280-91-6), (15.48) tolnifanide (304911-98-6), (15.49) triazoxide (72459-58-6), (15.50) trichlamide (70193-21-4), (15.51) zarilamid (84527-51-5), (15.52) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone (1003319-79-6) (WO 2008013622), (15.53) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.54) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.55) 1-(4-methoxyphenoxy)-3,3-dimethylbutan-2-yl 1H-imidazole-1-carboxylate (111227-17-9), (15.56) 2,3,5,6-tetrachloro-4-(methylsulfonyl)pyridine (13108-52-6), (15.57) 2,3-dibutyl-6-chlorothieno[2,3-d]pyrimidin-4(3H)-one (221451-58-7), (15.58) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.59) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.60) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.61) 2-butoxy-6-iodo-3-propyl-4H-chromen-4-one, (15.62) 2-chloro-5-[2-chloro-1-(2,6-difluoro-4-methoxyphenyl)-4-methyl-1H-imidazol-5-yl]pyridine, (15.63) 2-phenylphenol and salts (90-43-7), (15.64) 3,4,5-trichloropyridine-2,6-dicarbonitrile (17824-85-0), (15.65) 3-[5-(4-chlorophenyl)-2,3-dimethyl-1,2-oxazolidin-3-yl]pyridine, (15.66) 3-chloro-5-(4-chlorophenyl)-4-(2,6-difluorophenyl)-6-methylpyridazine, (15.67) 4-(4-chlorophenyl)-5-(2,6- difluorophenyl)-3,6-dimethylpyridazine, (15.68) 5-amino-1,3,4-thiadiazole-2-thiol, (15.69) 5-chloro-N'-phenyl-N'-(prop-2-yn-1-yl)thiophene-2-sulfonohydrazide (134-31-6), (15.70) 5-methyl-6-octyl[1,2,4]triazolo[1,5-a]pyrimidin-7-amine, (15.71) ethyl (2Z)-3-amino-2-cyano-3-phenylprop-2-enoate, (15.72) N-(4-chlorobenzyl)-3-[3-methoxy-4-(prop-2-yn-1-yloxy)phenyl]propanamide, (15.73) N-[(4-chlorophenyl)(cyano)methyl]-3-[3-methoxy-4-(prop-2-yn-1-yloxy)phenyl]propanamide, (15.74) N-[(5-bromo-3-chloropyridin-2-yl)methyl]-2,4-dichloropyridine-3-carboxamide, (15.75) N-[1-(5-bromo-3-chloropyridin-2-yl)ethyl]-2,4-dichloropyridine-3-carboxamide, (15.76) N-[1-(5-bromo-3-chloropyridin-2-yl)ethyl]-2-fluoro-4-iodopyridine-3-carboxamide, (15.77) N-{(E)-[(cyclopropylmethoxy)imino][6-(difluoromethoxy)-2,3-difluorophenyl]methyl}-2-phenylacetamide (221201-92-9), (15.78) N-{(Z)-[(cyclopropylmethoxy)imino][6-(difluoromethoxy)-2,3-difluorophenyl]methyl}-2-phenylacetamide (221201-92-9), (15.79) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.80) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.81) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5) (WO 2007014290), (15.82) pentyl {6-[({[(1-methyl-1H-tetrazol-5-yl)(phenyl)methylidene]amino}oxy)methyl]pyridin-2-yl}carbamate, (15.83) phenazine-1-carboxylic acid, (15.84) quinolin-8-ol (134-31-6) and (15.85) quinolin-8-ol sulfate (2:1) (134-31-6).

According to another object of the present invention, there is provided a method for controlling the phytopathogenic fungi of plants, crops or seeds, characterized in that an agronomically effective and substantially non-phytotoxic quantity of a fungicide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the fungicide composition which is the subject of the invention can be applied by means of various methods of treatment such as:

spraying onto the aerial parts of the said plants a liquid comprising one of the said compositions, dusting, the incorporation into the soil of granules or powders, spraying, around the said plants and in the case of trees injection or daubing, coating or film-coating the seeds of the said plants with the aid of a plant-protection mixture comprising one of the said compositions.

The method according to the invention can either be a curing, preventing or eradicating method. In this method, a composition used can be prepared beforehand by mixing the two or more active compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 2 to 200 g per 100 kilogram of seed, preferably from 3 to 150 g per 100 kilogram of seed;

for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., Actimidaceae sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilion-* aceae sp. (for instance soybean), *Solanaceae* sp. (for instance potatoes), *Chenopodiaceae* sp. (for instance beetroots); horticultural and forest crops; as well as genetically modified homologues of these crops.

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

Among the diseases of plants or crops that can be controlled by the method according to the invention, mention can be made of:

Powdery mildew diseases such as:
*Blumeria* diseases, caused for example by *Blumeria graminis*;
*Podosphaera* diseases, caused for example by *Podosphaera leucotricha*;
*Sphaerotheca* diseases, caused for example by *Sphaerotheca fuliginea*;
*Uncinula* diseases, caused for example by *Uncinula necator*;

Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondita*;
*Uromyces* diseases, caused for example by *Uromyces appendiculatus*;

Oomycete diseases such as:
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;
*Plasmopara* diseases, caused for example by *Plasmopara viticola*;
*Pseudoperonospora* diseases, caused for example by *Pseudoperonospora humuli* or *Pseudoperonospora cubensis*;
*Pythium* diseases, caused for example by *Pythium ultimum*;

Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus*;
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola*; *Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*;
*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incamata*;
*Venturia* diseases, caused for example by *Venturia inaequalis*;

Root and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;

Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;

Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;

Fruit rot and mould diseases such as:
*Aspergillus* diseases, caused for example by *Aspergillus flavus*;
*Botrytis* diseases, caused for example by *Botrytis cinerea*;

*Penicillium* diseases, caused for example by *Penicillium expansum;*
*Sclerotinia* diseases, caused for example by *Sclerotinia sclerotiorum;*
*Verticilium* diseases, caused for example by *Verticilium alboatrum;*
Seed and soilborne decay, mould, wilt, rot and damping-off diseases:
*Alternaria* diseases, caused for example by *Alternaria brassicicola*
*Aphanomyces* diseases, caused for example by *Aphanomyces euteiches*
*Ascochyta* diseases, caused for example by *Ascochyta lentis*
*Aspergillus* diseases, caused for example by *Aspergillus flavus*
*Cladosporium* diseases, caused for example by *Cladosporium herbarum*
*Cochliobolus* diseases, caused for example by *Cochliobolus sativus*
(Conidiaform: *Drechslera, Bipolaris* Syn: *Helminthosporium*);
*Colletotrichum* diseases, caused for example by *Colletotrichum coccodes;*
*Fusarium* diseases, caused for example by *Fusarium culmorum;*
*Gibberella* diseases, caused for example by *Gibberella zeae;*
*Macrophomina* diseases, caused for example by *Macrophomina phaseolina*
*Monographella* diseases, caused for example by *Monographella nivalis;*
*Penicillium* diseases, caused for example by *Penicillium expansum*
*Phoma* diseases, caused for example by *Phoma lingam*
*Phomopsis* diseases, caused for example by *Phomopsis sojae;*
*Phytophthora* diseases, caused for example by *Phytophthora cactorum;*
*Pyrenophora* diseases, caused for example by *Pyrenophora graminea*
*Pyricularia* diseases, caused for example by *Pyricularia oryzae;*
*Pythium* diseases, caused for example by *Pythium ultimum;*
*Rhizoctonia* diseases, caused for example by *Rhizoctonia solani;*
*Rhizopus* diseases, caused for example by *Rhizopus* oryzae
*Sclerotium* diseases, caused for example by *Sclerotium rolfsii;*
*Septoria* diseases, caused for example by *Septoria nodorum;*
*Typhula* diseases, caused for example by *Typhula incarnate;*
*Verticillium* diseases, caused for example by *Verticillium dahliae;*
Canker, broom and dieback diseases such as:
*Nectria* diseases, caused for example by *Nectria galligena;*
Blight diseases such as:
*Monilinia* diseases, caused for example by *Monilinia laxa;*
Leaf blister or leaf curl diseases such as:
*Taphrina* diseases, caused for example by *Taphrina deformans;*
Decline diseases of wooden plants such as:
Esca diseases, caused for example by *Phaemoniella clamydospora;*
*Eutypa* dyeback, caused for example by *Eutypa lata;*
Dutch elm disease, caused for example by *Ceratocystsc ulmi;*
Diseases of flowers and Seeds such as:
*Botrytis* diseases, caused for example by *Botrytis cinerea;*
Diseases of tubers such as:
*Rhizoctonia* diseases, caused for example by *Rhizoctonia solani*
*Helminthosporium* diseases, caused for example by *Helminthosporium* solani.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229, 072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the to bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988),263, 4280-4289), or an *Eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637, 489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that are made tolerant to the herbicides inhibiting the enzyme hydroxyphenylpyruvatedioxygenase (HPPD).

Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, to triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. No. 5,605,011, U.S. Pat. No. 5,378,824, U.S. Pat. No. 5,141,870, and U.S. Pat. No. 5,013,659. The production of sulfonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance. An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants as described in WO 2000/004173 or WO2006/045633 or PCT/EP07/004,142.

b. plants which contain a stress tolerance enhancing transgene capable of reducing the expression and/or the activity of the PARG encoding genes of the plants or plants cells, as described e.g. in WO 2004/090140.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002,433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908, 975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 1998/000549 b) Plants, such as cotton plants, containing an altered form of rsw2 or rsw3 homologous nucleic acids as described in WO2004/053219 c) Plants, such as cotton plants, with increased expression of sucrose phosphate synthase as described in WO 2001/017333 d) Plants, such as cotton plants, with increased expression of sucrose synthase as described in WO02/45485 e) Plants, such as cotton plants, wherein the timing of the plasmodesmatal gating at the basis of the fiber cell is altered, e.g. through downregulation of fiberselective β 1,3-glucanase as described in WO2005/017157 f) Plants, such as cotton plants, having fibers with altered reactivity, e.g. through the expression of N-acteylglucosaminetransferase gene including nodC and chitinsynthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947 b) Plants such as oilseed rape plants, producing oil having a low linolenic acid content as described in U.S. Pat. No. 6,270,828, U.S. Pat. No. 6,169,190 or U.S. Pat. No. 5,965,755 c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for to example maize, cotton, soya bean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp browse.aspx and http://www.agbios.com/dbase.php).

The compounds according to the invention can also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

The various aspects of the invention will now be illustrated with reference to the following table 1 of compound examples and the following preparation or efficacy examples.

The following table 1 illustrates in a non limiting manner examples of compounds according to the invention.

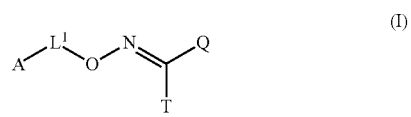

In table 1, M+H (Apcl+) means the molecular ion peak plus 1 a.m.u. (atomic mass unit) as observed in mass spectroscopy via positive atmospheric pressure chemical ionisation.

In table 1, we use the following abbreviations for specified claimed elements "A" of the generic structure (I) of the invention:

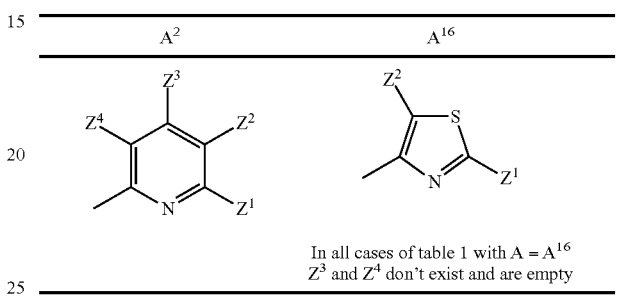

In all cases of table 1 with A = $A^{16}$
$Z^3$ and $Z^4$ don't exist and are empty

TABLE 1

| Ex. | Q | T | L1 | An | Z1 | Z2 | Z3 | Z4 | logP | Mass (M + H) |
|---|---|---|---|---|---|---|---|---|---|---|
| 1 | phenyl | cyano | CH2 | A2 | (tert-butoxycarbonyl)amino | H | H | H | 4.64 | 353 |
| 2 | phenyl | cyano | CH2 | A2 | [(pentyloxy)carbonyl]amino | H | H | H | | |
| 3 | phenyl | cyano | CH2 | A2 | [(but-3-yn-1-yloxy)carbonyl]amino | H | H | H | 3.67 | 349 |
| 4 | phenyl | cyano | CH2 | A2 | [(pent-4-yn-2-yloxy)carbonyl]amino | H | H | H | | |
| 5 | phenyl | cyano | CH2 | A2 | [(hex-5-yn-1-yloxy)carbonyl]amino | H | H | H | | |
| 6 | phenyl | cyano | CH2 | A2 | benzoylamino | H | H | H | | |
| 7 | phenyl | cyano | CH2 | A2 | (phenylacetyl)amino | H | H | H | | |
| 8 | phenyl | cyano | CH2 | A2 | (phenoxyacetyl)amino | H | H | H | | |
| 9 | phenyl | cyano | CH2 | A2 | [(2-phenylethoxy)carbonyl]amino | H | H | H | | |
| 10 | phenyl | cyano | CH2 | A2 | [(cyclohexyloxy)acetyl]amino | H | H | H | | |
| 11 | phenyl | cyano | CH2 | A2 | (3,4-dihydro-2H-chromen-2-ylcarbonyl)amino | H | H | H | | |
| 12 | phenyl | cyano | CH2 | A2 | (2,3-dihydro-1,4-benzodioxin-2-ylcarbonyl)amino | H | H | H | | |
| 13 | phenyl | cyano | CH2 | A16 | (tert-butoxycarbonyl)amino | H | | | | |
| 14 | phenyl | cyano | CH2 | A16 | [(pentyloxy)carbonyl]amino | H | | | | |
| 15 | phenyl | cyano | CH2 | A16 | [(but-3-yn-1-yloxy)carbonyl]amino | H | | | | |
| 16 | phenyl | cyano | CH2 | A16 | [(pent-4-yn-2-yloxy)carbonyl]amino | H | | | | |
| 17 | phenyl | cyano | CH2 | A16 | [(hex-5-yn-1-yloxy)carbonyl]amino | H | | | | |
| 18 | phenyl | cyano | CH2 | A16 | benzoylamino | H | | | | |
| 19 | phenyl | cyano | CH2 | A16 | (phenylacetyl)amino | H | | | | |
| 20 | phenyl | cyano | CH2 | A16 | (phenoxyacetyl)amino | H | | | | |
| 21 | phenyl | cyano | CH2 | A16 | [(2-phenylethoxy)carbonyl]amino | H | | | | |
| 22 | phenyl | cyano | CH2 | A16 | [(cyclohexyloxy)acetyl]amino | H | | | | |
| 23 | phenyl | cyano | CH2 | A16 | (3,4-dihydro-2H-chromen-2-ylcarbonyl)amino | H | | | | |
| 24 | phenyl | cyano | CH2 | A16 | (2,3-dihydro-1,4-benzodioxin-2-ylcarbonyl)amino | H | | | | |
| 25 | phenyl | methoxycarbonyl | CH2 | A2 | amino | H | H | H | 1.32 | 286 |
| 26 | phenyl | methoxycarbonyl | CH2 | A2 | (tert-butoxycarbonyl)amino | H | H | H | 4.20 | 386 |
| 27 | phenyl | methoxycarbonyl | CH2 | A2 | [(pentyloxy)carbonyl]amino | H | H | H | 3.69 | 400 |
| 28 | phenyl | methoxycarbonyl | CH2 | A2 | [(but-3-yn-1-yloxy)carbonyl]amino | H | H | H | 3.48 | 382 |
| 29 | phenyl | methoxycarbonyl | CH2 | A2 | [(pent-4-yn-2-yloxy)carbonyl]amino | H | H | H | | |
| 30 | phenyl | methoxycarbonyl | CH2 | A2 | [(hex-5-yn-1-yloxy)carbonyl]amino | H | H | H | | |
| 31 | phenyl | methoxycarbonyl | CH2 | A2 | benzoylamino | H | H | H | | |
| 32 | phenyl | methoxycarbonyl | CH2 | A2 | (phenylacetyl)amino | H | H | H | | |
| 33 | phenyl | methoxycarbonyl | CH2 | A2 | (phenoxyacetyl)amino | H | H | H | | |
| 34 | phenyl | methoxycarbonyl | CH2 | A2 | [(2-phenylethoxy)carbonyl]amino | H | H | H | | |
| 35 | phenyl | methoxycarbonyl | CH2 | A2 | [(cyclohexyloxy)acetyl]amino | H | H | H | | |
| 36 | phenyl | methoxycarbonyl | CH2 | A2 | (3,4-dihydro-2H-chromen-2-ylcarbonyl)amino | H | H | H | | |
| 37 | phenyl | methoxycarbonyl | CH2 | A2 | (2,3-dihydro-1,4-benzodioxin-2-ylcarbonyl)amino | H | H | H | 4.16 | 448 |

TABLE 1-continued

| Ex. | Q | T | L1 | An | Z1 | Z2 | Z3 | Z4 | logP | Mass (M + H) |
|---|---|---|---|---|---|---|---|---|---|---|
| 38 | phenyl | methoxycarbonyl | CH2 | A2 | [difluoro(phenoxy)acetyl]amino | H | H | H | 4.41 | 456 |
| 39 | phenyl | methoxycarbonyl | CH2 | A2 | [(4-methoxyphenyl)acetyl]amino | H | H | H | 3.69 | 434 |
| 40 | phenyl | methoxycarbonyl | CH2 | A2 | (3-fluorobenzoyl)amino | H | H | H | 3.94 | 408 |
| 41 | phenyl | methoxycarbonyl | CH2 | A2 | (3-phenylpropyl)amino | H | H | H | 2.60 | 404 |
| 42 | phenyl | methoxycarbonyl | CH2 | A2 | [(but-3-en-1-yloxy)carbonyl]amino | H | H | H | 3.94 | 384 |
| 43 | phenyl | methoxycarbonyl | CH2 | A2 | (2-thienylcarbonyl)amino | H | H | H | 3.67 | 396 |
| 44 | phenyl | methoxycarbonyl | CH2 | A2 | (2-cyclohexylethyl)amino | H | H | H | 3.04 | 396 |
| 45 | phenyl | methoxycarbonyl | CH2 | A2 | [(but-2-yn-1-yloxy)carbonyl]amino | H | H | H | 3.67 | 382 |
| 46 | phenyl | methoxycarbonyl | CH2 | A2 | [(hexyloxy)carbonyl]amino | H | H | H | 5.14 | 414 |
| 47 | phenyl | methoxycarbonyl | CH2 | A16 | (tert-butoxycarbonyl)amino | H | | | | |
| 48 | phenyl | methoxycarbonyl | CH2 | A16 | [(pentyloxy)carbonyl]amino | H | | | | |
| 49 | phenyl | methoxycarbonyl | CH2 | A16 | [(but-3-yn-1-yloxy)carbonyl]amino | H | | | | |
| 50 | phenyl | methoxycarbonyl | CH2 | A16 | [(pent-4-yn-2-yloxy)carbonyl]amino | H | | | | |
| 51 | phenyl | methoxycarbonyl | CH2 | A16 | [(hex-5-yn-1-yloxy)carbonyl]amino | H | | | | |
| 52 | phenyl | methoxycarbonyl | CH2 | A16 | benzoylamino | H | | | | |
| 53 | phenyl | methoxycarbonyl | CH2 | A16 | (phenylacetyl)amino | H | | | | |
| 54 | phenyl | methoxycarbonyl | CH2 | A16 | (phenoxyacetyl)amino | H | | | | |
| 55 | phenyl | methoxycarbonyl | CH2 | A16 | [(2-phenylethoxy)carbonyl]amino | H | | | | |
| 56 | phenyl | methoxycarbonyl | CH2 | A16 | [(cyclohexyloxy)acetyl]amino | H | | | | |
| 57 | phenyl | methoxycarbonyl | CH2 | A16 | (3,4-dihydro-2H-chromen-2-ylcarbonyl)amino | H | | | | |
| 58 | phenyl | methoxycarbonyl | CH2 | A16 | (2,3-dihydro-1,4-benzodioxin-2-ylcarbonyl)amino | H | | | | |
| 59 | phenyl | ethoxycarbonyl | CH2 | A16 | (2,2-dimethylpropanoyl)amino | H | | | | |
| 60 | phenyl | methylcarbamoyl | CH2 | A2 | amino | H | H | H | 0.65 | 285 |
| 61 | 4-benzyloxy phenyl | methylcarbamoyl | CH2 | A2 | amino | H | H | H | 1.17 | 391 |
| 62 | phenyl | methylcarbamoyl | CH2 | A2 | (tert-butoxycarbonyl)amino | H | H | H | 2.88 | 385 |
| 63 | phenyl | methylcarbamoyl | CH2 | A2 | [(pentyloxy)carbonyl]amino | H | H | H | | |
| 64 | 4-Benzyloxy phenyl | methylcarbamoyl | CH2 | A2 | [(pentyloxy)carbonyl]amino | H | H | H | 2.65 | 505 |
| 65 | 4-Phenoxy phenyl | methylcarbamoyl | CH2 | A2 | [(pentyloxy)carbonyl]amino | H | H | H | 2.64 | 491 |
| 66 | phenyl | methylcarbamoyl | CH2 | A2 | [(but-3-yn-1-yloxy)carbonyl]amino | H | H | H | 3.48 | 399 |
| 67 | phenyl | methylcarbamoyl | CH2 | A2 | [(pent-4-yn-2-yloxy)carbonyl]amino | H | H | H | | |
| 68 | phenyl | methylcarbamoyl | CH2 | A2 | [(hex-5-yn-1-yloxy)carbonyl]amino | H | H | H | | |
| 69 | phenyl | methylcarbamoyl | CH2 | A2 | benzoylamino | H | H | H | | |
| 70 | phenyl | methylcarbamoyl | CH2 | A2 | (phenylacetyl)amino | H | H | H | | |
| 71 | phenyl | methylcarbamoyl | CH2 | A2 | (phenoxyacetyl)amino | H | H | H | | |
| 72 | phenyl | methylcarbamoyl | CH2 | A2 | [(2-phenylethoxy)carbonyl]amino | H | H | H | | |
| 73 | phenyl | methylcarbamoyl | CH2 | A2 | [(cyclohexyloxy)acetyl]amino | H | H | H | | |
| 74 | phenyl | methylcarbamoyl | CH2 | A2 | (3,4-dihydro-2H-chromen-2-ylcarbonyl)amino | H | H | H | | |
| 75 | phenyl | methylcarbamoyl | CH2 | A2 | (2,3-dihydro-1,4-benzodioxin-2-ylcarbonyl)amino | H | H | H | 3.06 | 447 |
| 76 | phenyl | methylcarbamoyl | CH2 | A2 | [difluoro(phenoxy)acetyl]amino | H | H | H | 3.35 | 455 |
| 77 | phenyl | methylcarbamoyl | CH2 | A2 | [(4-methoxyphenyl)acetyl]amino | H | H | H | 2.66 | 433 |
| 78 | phenyl | methylcarbamoyl | CH2 | A2 | (3-fluorobenzoyl)amino | H | H | H | 2.84 | 407 |
| 79 | phenyl | methylcarbamoyl | CH2 | A2 | (3-phenylpropyl)amino | H | H | H | 1.94 | 403 |
| 80 | phenyl | methylcarbamoyl | CH2 | A2 | [(but-3-en-1-yloxy)carbonyl]amino | H | H | H | 2.77 | 383 |
| 81 | phenyl | methylcarbamoyl | CH2 | A2 | (2-thienylcarbonyl)amino | H | H | H | 2.57 | 395 |
| 82 | phenyl | methylcarbamoyl | CH2 | A2 | (2-cyclohexylethyl)amino | H | H | H | 2.23 | 395 |
| 83 | phenyl | methylcarbamoyl | CH2 | A2 | [(but-2-yn-1-yloxy)carbonyl]amino | H | H | H | 2.59 | 381 |
| 84 | phenyl | methylcarbamoyl | CH2 | A2 | [(hexyloxy)carbonyl]amino | H | H | H | 3.48 | 413 |
| 85 | phenyl | methylcarbamoyl | CH2 | A16 | (tert-butoxycarbonyl)amino | H | | | | |
| 86 | phenyl | methylcarbamoyl | CH2 | A16 | [(pentyloxy)carbonyl]amino | H | | | | |
| 87 | phenyl | methylcarbamoyl | CH2 | A16 | [(but-3-yn-1-yloxy)carbonyl]amino | H | | | | |
| 88 | phenyl | methylcarbamoyl | CH2 | A16 | [(pent-4-yn-2-yloxy)carbonyl]amino | H | | | | |
| 89 | phenyl | methylcarbamoyl | CH2 | A16 | [(hex-5-yn-1-yloxy)carbonyl]amino | H | | | | |
| 90 | phenyl | methylcarbamoyl | CH2 | A16 | benzoylamino | H | | | | |
| 91 | phenyl | methylcarbamoyl | CH2 | A16 | (phenylacetyl)amino | H | | | | |
| 92 | phenyl | methylcarbamoyl | CH2 | A16 | (phenoxyacetyl)amino | H | | | | |
| 93 | phenyl | methylcarbamoyl | CH2 | A16 | [(2-phenylethoxy)carbonyl]amino | H | | | | |
| 94 | phenyl | methylcarbamoyl | CH2 | A16 | [(cyclohexyloxy)acetyl]amino | H | | | | |
| 95 | phenyl | methylcarbamoyl | CH2 | A16 | (3,4-dihydro-2H-chromen-2-ylcarbonyl)amino | H | | | | |
| 96 | phenyl | methylcarbamoyl | CH2 | A16 | (2,3-dihydro-1,4-benzodioxin-2-ylcarbonyl)amino | H | | | | |
| 97 | phenyl | dimethylcarbamoyl | CH2 | A2 | amino | H | H | H | 1.10 | 299 |
| 98 | phenyl | dimethylcarbamoyl | CH2 | A2 | (tert-butoxycarbonyl)amino | H | H | H | 3.37 | 399 |
| 99 | phenyl | dimethylcarbamoyl | CH2 | A2 | [(pentyloxy)carbonyl]amino | H | H | H | 3.96 | 413 |
| 100 | phenyl | dimethylcarbamoyl | CH2 | A2 | [(but-3-yn-1-yloxy)carbonyl]amino | H | H | H | 1.83 | 395 |
| 101 | phenyl | dimethylcarbamoyl | CH2 | A2 | [(pent-4-yn-2-yloxy)carbonyl]amino | H | H | H | 3.07 | 409 |
| 102 | phenyl | dimethylcarbamoyl | CH2 | A2 | [(hex-5-yn-1-yloxy)carbonyl]amino | H | H | H | | |
| 103 | phenyl | dimethylcarbamoyl | CH2 | A2 | benzoylamino | H | H | H | | |
| 104 | phenyl | dimethylcarbamoyl | CH2 | A2 | (phenylacetyl)amino | H | H | H | | |
| 105 | phenyl | dimethylcarbamoyl | CH2 | A2 | (phenoxyacetyl)amino | H | H | H | | |

TABLE 1-continued

| Ex. | Q | T | L1 | An | Z1 | Z2 | Z3 | Z4 | logP | Mass (M + H) |
|---|---|---|---|---|---|---|---|---|---|---|
| 106 | phenyl | dimethylcarbamoyl | CH2 | A2 | [(2-phenylethoxy)carbonyl]amino | H | H | H | | |
| 107 | phenyl | dimethylcarbamoyl | CH2 | A2 | [(cyclohexyloxy)acetyl]amino | H | H | H | | |
| 108 | phenyl | dimethylcarbamoyl | CH2 | A2 | (3,4-dihydro-2H-chromen-2-ylcarbonyl)amino | H | H | H | | |
| 109 | phenyl | dimethylcarbamoyl | CH2 | A2 | (2,3-dihydro-1,4-benzodioxin-2-ylcarbonyl)amino | H | H | H | 3.42 | 461 |
| 110 | phenyl | dimethylcarbamoyl | CH2 | A2 | [difluoro(phenoxy)acetyl]amino | H | H | H | 3.73 | 469 |
| 111 | phenyl | dimethylcarbamoyl | CH2 | A2 | (2-phenoxypropanoyl)amino | H | H | H | 3.50 | 447 |
| 112 | phenyl | dimethylcarbamoyl | CH2 | A2 | [(4-methoxyphenyl)acetyl]amino | H | H | H | 3.00 | 447 |
| 113 | phenyl | dimethylcarbamoyl | CH2 | A2 | (3-fluorobenzoyl)amino | H | H | H | 3.23 | 421 |
| 114 | phenyl | dimethylcarbamoyl | CH2 | A2 | (4-chlorobenzoyl)amino | H | H | H | 3.57 | 437 |
| 115 | phenyl | dimethylcarbamoyl | CH2 | A2 | [(2-phenoxyethoxy)carbonyl]amino | H | H | H | 3.48 | 463 |
| 116 | phenyl | dimethylcarbamoyl | CH2 | A2 | [(but-3-en-1-yloxy)carbonyl]amino | H | H | H | 3.19 | 397 |
| 117 | phenyl | dimethylcarbamoyl | CH2 | A2 | [(4-methoxyphenyloxy)carbonyl]amino | H | H | H | 3.25 | 449 |
| 118 | phenyl | dimethylcarbamoyl | CH2 | A16 | (tert-butoxycarbonyl)amino | H | | | | |
| 119 | phenyl | dimethylcarbamoyl | CH2 | A16 | [(pentyloxy)carbonyl]amino | H | | | | |
| 120 | phenyl | dimethylcarbamoyl | CH2 | A16 | [(but-3-yn-1-yloxy)carbonyl]amino | H | | | 2.84 | |
| 121 | phenyl | dimethylcarbamoyl | CH2 | A16 | [(pent-4-yn-2-yloxy)carbonyl]amino | H | | | 2.84 | 415 |
| 122 | phenyl | dimethylcarbamoyl | CH2 | A16 | [(hex-5-yn-1-yloxy)carbonyl]amino | H | | | 3.06 | 429 |
| 123 | phenyl | dimethylcarbamoyl | CH2 | A16 | benzoylamino | H | | | | |
| 124 | phenyl | dimethylcarbamoyl | CH2 | A16 | (phenylacetyl)amino | H | | | | |
| 125 | phenyl | dimethylcarbamoyl | CH2 | A16 | (phenoxyacetyl)amino | H | | | | |
| 126 | phenyl | dimethylcarbamoyl | CH2 | A16 | [(2-phenylethoxy)carbonyl]amino | H | | | | |
| 127 | phenyl | dimethylcarbamoyl | CH2 | A16 | [(cyclohexyloxy)acetyl]amino | H | | | | |
| 128 | phenyl | dimethylcarbamoyl | CH2 | A16 | (3,4-dihydro-2H-chromen-2-ylcarbonyl)amino | H | | | | |
| 129 | phenyl | dimethylcarbamoyl | CH2 | A16 | (2,3-dihydro-1,4-benzodioxin-2-ylcarbonyl)amino | H | | | 3.15 | 467 |
| 130 | phenyl | dimethylcarbamoyl | CH2 | A16 | (2-phenoxypropanoyl)amino | H | | | 3.21 | 453 |
| 131 | phenyl | dimethylcarbamoyl | CH2 | A16 | [(4-methoxyphenyl)acetyl]amino | H | | | 2.88 | 453 |
| 132 | phenyl | dimethylcarbamoyl | CH2 | A16 | (4-chlorobenzoyl)amino | H | | | 3.41 | 443 |
| 133 | phenyl | dimethylcarbamoyl | CH2 | A16 | [(2-phenoxyethoxy)carbonyl]amino | H | | | 3.27 | 469 |
| 134 | phenyl | dimethylcarbamoyl | CH2 | A16 | (4-methoxybenzoyl)amino | H | | | 2.84 | 439 |
| 135 | phenyl | ethyl(methyl)carbamoyl | CH2 | A2 | [(pent-4-yn-2-yloxy)carbonyl]amino | H | H | H | 3.31 | 423 |
| 136 | phenyl | ethyl(methyl)carbamoyl | CH2 | A2 | (2-phenoxypropanoyl)amino | H | H | H | 3.78 | 461 |
| 137 | phenyl | ethyl(methyl)carbamoyl | CH2 | A2 | [(4-methoxyphenyl)acetyl]amino | H | H | H | 3.23 | 461 |
| 138 | phenyl | ethyl(methyl)carbamoyl | CH2 | A2 | [(hex-5-yn-1-yloxy)carbonyl]amino | H | H | H | 3.35 | 437 |
| 139 | phenyl | ethyl(methyl)carbamoyl | CH2 | A2 | (2,3-dihydro-1,4-benzodioxin-2-ylcarbonyl)amino | H | H | H | 3.69 | 475 |
| 140 | phenyl | ethyl(methyl)carbamoyl | CH2 | A2 | (4-chlorobenzoyl)amino | H | H | H | 3.85 | 451 |
| 141 | phenyl | ethyl(methyl)carbamoyl | CH2 | A2 | [(2-phenoxyethoxy)carbonyl]amino | H | H | H | 3.76 | 477 |
| 142 | phenyl | ethyl(methyl)carbamoyl | CH2 | A2 | [(tert-butyloxy)carbonyl]amino | H | H | H | 3.72 | 413 |
| 143 | phenyl | ethyl(methyl)carbamoyl | CH2 | A2 | [(but-3-yn-1-yloxy)carbonyl]amino | H | H | H | 3.04 | 409 |
| 144 | phenyl | ethyl(methyl)carbamoyl | CH2 | A16 | amino | H | | | 1.34 | 319 |
| 145 | phenyl | ethyl(methyl)carbamoyl | CH2 | A16 | [(pent-4-yn-2-yloxy)carbonyl]amino | H | | | 3.09 | 429 |
| 146 | phenyl | ethyl(methyl)carbamoyl | CH2 | A16 | (2-phenoxypropanoyl)amino | H | | | 3.48 | 467 |
| 147 | phenyl | ethyl(methyl)carbamoyl | CH2 | A16 | [(4-methoxyphenyl)acetyl]amino | H | | | 3.09 | 467 |
| 148 | phenyl | ethyl(methyl)carbamoyl | CH2 | A16 | [(hex-5-yn-1-yloxy)carbonyl]amino | H | | | 3.29 | 443 |
| 149 | phenyl | ethyl(methyl)carbamoyl | CH2 | A16 | (2,3-dihydro-1,4-benzodioxin-2-ylcarbonyl)amino | H | | | 3.39 | 481 |
| 150 | phenyl | ethyl(methyl)carbamoyl | CH2 | A16 | (4-chlorobenzoyl)amino | H | | | 3.69 | 457 |
| 151 | phenyl | ethyl(methyl)carbamoyl | CH2 | A16 | [(2-phenoxyethoxy)carbonyl]amino | H | | | 3.48 | 483 |
| 152 | phenyl | ethyl(methyl)carbamoyl | CH2 | A16 | [(but-3-yn-1-yloxy)carbonyl]amino | H | | | 2.80 | 415 |
| 153 | phenyl | methoxycarbamoyl | CH2 | A2 | (tert-butoxycarbonyl)amino | H | H | H | | |
| 154 | phenyl | methoxycarbamoyl | CH2 | A2 | [(pentyloxy)carbonyl]amino | H | H | H | | |
| 155 | phenyl | methoxycarbamoyl | CH2 | A2 | [(but-3-yn-1-yloxy)carbonyl]amino | H | H | H | | |
| 156 | phenyl | methoxycarbamoyl | CH2 | A2 | [(pent-4-yn-2-yloxy)carbonyl]amino | H | H | H | | |
| 157 | phenyl | methoxycarbamoyl | CH2 | A2 | [(hex-5-yn-1-yloxy)carbonyl]amino | H | H | H | | |
| 158 | phenyl | methoxycarbamoyl | CH2 | A2 | benzoylamino | H | H | H | | |
| 159 | phenyl | methoxycarbamoyl | CH2 | A2 | (phenylacetyl)amino | H | H | H | | |
| 160 | phenyl | methoxycarbamoyl | CH2 | A2 | (phenoxyacetyl)amino | H | H | H | | |
| 161 | phenyl | methoxycarbamoyl | CH2 | A2 | [(2-phenylethoxy)carbonyl]amino | H | H | H | | |
| 162 | phenyl | methoxycarbamoyl | CH2 | A2 | [(cyclohexyloxy)acetyl]amino | H | H | H | | |
| 163 | phenyl | methoxycarbamoyl | CH2 | A2 | (3,4-dihydro-2H-chromen-2-ylcarbonyl)amino | H | H | H | | |
| 164 | phenyl | methoxycarbamoyl | CH2 | A2 | (2,3-dihydro-1,4-benzodioxin-2-ylcarbonyl)amino | H | H | H | | |
| 165 | phenyl | methoxycarbamoyl | CH2 | A16 | (tert-butoxycarbonyl)amino | H | | | | |
| 166 | phenyl | methoxycarbamoyl | CH2 | A16 | [(pentyloxy)carbonyl]amino | H | | | | |
| 167 | phenyl | methoxycarbamoyl | CH2 | A16 | [(but-3-yn-1-yloxy)carbonyl]amino | H | | | | |
| 168 | phenyl | methoxycarbamoyl | CH2 | A16 | [(pent-4-yn-2-yloxy)carbonyl]amino | H | | | | |
| 169 | phenyl | methoxycarbamoyl | CH2 | A16 | [(hex-5-yn-1-yloxy)carbonyl]amino | H | | | | |
| 170 | phenyl | methoxycarbamoyl | CH2 | A16 | benzoylamino | H | | | | |
| 171 | phenyl | methoxycarbamoyl | CH2 | A16 | (phenylacetyl)amino | H | | | | |
| 172 | phenyl | methoxycarbamoyl | CH2 | A16 | (phenoxyacetyl)amino | H | | | | |
| 173 | phenyl | methoxycarbamoyl | CH2 | A16 | [(2-phenylethoxy)carbonyl]amino | H | | | | |

TABLE 1-continued

| Ex. | Q | T | L1 | An | Z1 | Z2 | Z3 | Z4 | logP | Mass (M + H) |
|---|---|---|---|---|---|---|---|---|---|---|
| 174 | phenyl | methoxycarbamoyl | CH2 | A16 | [(cyclohexyloxy)acetyl]amino | H | | | | |
| 175 | phenyl | methoxycarbamoyl | CH2 | A16 | (3,4-dihydro-2H-chromen-2-ylcarbonyl)amino | H | | | | |
| 176 | phenyl | methoxycarbamoyl | CH2 | A16 | (2,3-dihydro-1,4-benzodioxin-2-ylcarbonyl)amino | H | | | | |
| 177 | phenyl | methoxy(methyl)carbamoyl | CH2 | A2 | (tert-butoxycarbonyl)amino | H | H | H | | |
| 178 | phenyl | methoxy(methyl)carbamoyl | CH2 | A2 | [(pentyloxy)carbonyl]amino | H | H | H | | |
| 179 | phenyl | methoxy(methyl)carbamoyl | CH2 | A2 | [(but-3-yn-1-yloxy)carbonyl]amino | H | H | H | | |
| 180 | phenyl | methoxy(methyl)carbamoyl | CH2 | A2 | [(pent-4-yn-2-yloxy)carbonyl]amino | H | H | H | | |
| 181 | phenyl | methoxy(methyl)carbamoyl | CH2 | A2 | [(hex-5-yn-1-yloxy)carbonyl]amino | H | H | H | | |
| 182 | phenyl | methoxy(methyl)carbamoyl | CH2 | A2 | benzoylamino | H | H | H | | |
| 183 | phenyl | methoxy(methyl)carbamoyl | CH2 | A2 | (phenylacetyl)amino | H | H | H | | |
| 184 | phenyl | methoxy(methyl)carbamoyl | CH2 | A2 | (phenoxyacetyl)amino | H | H | H | | |
| 185 | phenyl | methoxy(methyl)carbamoyl | CH2 | A2 | [(2-phenylethoxy)carbonyl]amino | H | H | H | | |
| 186 | phenyl | methoxy(methyl)carbamoyl | CH2 | A2 | [(cyclohexyloxy)acetyl]amino | H | H | H | | |
| 187 | phenyl | methoxy(methyl)carbamoyl | CH2 | A2 | (3,4-dihydro-2H-chromen-2-ylcarbonyl)amino | H | H | H | | |
| 188 | phenyl | methoxy(methyl)carbamoyl | CH2 | A2 | (2,3-dihydro-1,4-benzodioxin-2-ylcarbonyl)amino | H | H | H | | |
| 189 | phenyl | methoxy(methyl)carbamoyl | CH2 | A16 | (tert-butoxycarbonyl)amino | H | | | | |
| 190 | phenyl | methoxy(methyl)carbamoyl | CH2 | A16 | [(pentyloxy)carbonyl]amino | H | | | | |
| 191 | phenyl | methoxy(methyl)carbamoyl | CH2 | A16 | [(but-3-yn-1-yloxy)carbonyl]amino | H | | | | |
| 192 | phenyl | methoxy(methyl)carbamoyl | CH2 | A16 | [(pent-4-yn-2-yloxy)carbonyl]amino | H | | | | |
| 193 | phenyl | methoxy(methyl)carbamoyl | CH2 | A16 | [(hex-5-yn-1-yloxy)carbonyl]amino | H | | | | |
| 194 | phenyl | methoxy(methyl)carbamoyl | CH2 | A16 | benzoylamino | H | | | | |
| 195 | phenyl | methoxy(methyl)carbamoyl | CH2 | A16 | (phenylacetyl)amino | H | | | | |
| 196 | phenyl | methoxy(methyl)carbamoyl | CH2 | A16 | (phenoxyacetyl)amino | H | | | | |
| 197 | phenyl | methoxy(methyl)carbamoyl | CH2 | A16 | [(2-phenylethoxy)carbonyl]amino | H | | | | |
| 198 | phenyl | methoxy(methyl)carbamoyl | CH2 | A16 | [(cyclohexyloxy)acetyl]amino | H | | | | |
| 199 | phenyl | methoxy(methyl)carbamoyl | CH2 | A16 | (3,4-dihydro-2H-chromen-2-ylcarbonyl)amino | H | | | | |
| 200 | phenyl | methoxy(methyl)carbamoyl | CH2 | A16 | (2,3-dihydro-1,4-benzodioxin-2-ylcarbonyl)amino | H | | | | |
| 201 | phenyl | ethoxy(methyl)carbamoyl | CH2 | A2 | [(tert-butyloxy)carbonyl]amino | H | H | H | 2.38 | 429 |
| 202 | phenyl | ethoxy(methyl)carbamoyl | CH2 | A2 | [(hex-5-yn-1-yloxy)carbonyl]amino | H | H | H | 3.71 | 453 |
| 203 | phenyl | ethoxy(methyl)carbamoyl | CH2 | A2 | (2,3-dihydro-1,4-benzodioxin-2-ylcarbonyl)amino | H | H | H | 3.83 | 491 |
| 204 | phenyl | ethoxy(methyl)carbamoyl | CH2 | A2 | (4-chlorobenzoyl)amino | H | H | H | 4.01 | 467 |
| 205 | phenyl | ethoxy(methyl)carbamoyl | CH2 | A2 | (2-phenoxypropanoyl)amino | H | H | H | 3.94 | 477 |
| 206 | phenyl | ethoxy(methyl)carbamoyl | CH2 | A2 | [(4-methoxyphenyl)acetyl]amino | H | H | H | 3.37 | 477 |
| 207 | phenyl | ethoxy(methyl)carbamoyl | CH2 | A2 | [(2-phenoxyethoxy)carbonyl]amino | H | H | H | 3.89 | 493 |
| 208 | phenyl | ethoxy(methyl)carbamoyl | CH2 | A16 | amino | H | | | 1.35 | 335 |
| 209 | phenyl | ethoxy(methyl)carbamoyl | CH2 | A16 | [(2-phenoxyethoxy)carbonyl]amino | H | | | 3.62 | 499 |
| 210 | phenyl | ethoxy(methyl)carbamoyl | CH2 | A16 | [(4-methoxyphenyl)acetyl]amino | H | | | 3.23 | 483 |
| 211 | phenyl | ethoxy(methyl)carbamoyl | CH2 | A16 | [(hex-5-yn-1-yloxy)carbonyl]amino | H | | | 3.44 | 459 |
| 212 | phenyl | (2,2-dimethylhydrazino)carbonyl | CH2 | A2 | (tert-butoxycarbonyl)amino | H | H | H | | |
| 213 | phenyl | (2,2-dimethylhydrazino)carbonyl | CH2 | A2 | [(pentyloxy)carbonyl]amino | H | H | H | | |
| 214 | phenyl | (2,2-dimethylhydrazino)carbonyl | CH2 | A2 | [(but-3-yn-1-yloxy)carbonyl]amino | H | H | H | | |
| 215 | phenyl | (2,2-dimethylhydrazino)carbonyl | CH2 | A2 | [(pent-4-yn-2-yloxy)carbonyl]amino | H | H | H | | |
| 216 | phenyl | (2,2-dimethylhydrazino)carbonyl | CH2 | A2 | [(hex-5-yn-1-yloxy)carbonyl]amino | H | H | H | | |
| 217 | phenyl | (2,2-dimethylhydrazino)carbonyl | CH2 | A2 | benzoylamino | H | H | H | | |
| 218 | phenyl | (2,2-dimethylhydrazino)carbonyl | CH2 | A2 | (phenylacetyl)amino | H | H | H | | |
| 219 | phenyl | (2,2-dimethylhydrazino)carbonyl | CH2 | A2 | (phenoxyacetyl)amino | H | H | H | | |
| 220 | phenyl | (2,2-dimethylhydrazino)carbonyl | CH2 | A2 | [(2-phenylethoxy)carbonyl]amino | H | H | H | | |
| 221 | phenyl | (2,2-dimethylhydrazino)carbonyl | CH2 | A2 | [(cyclohexyloxy)acetyl]amino | H | H | H | | |
| 222 | phenyl | (2,2-dimethylhydrazino)carbonyl | CH2 | A2 | (3,4-dihydro-2H-chromen-2-ylcarbonyl)amino | H | H | H | | |
| 223 | phenyl | (2,2-dimethylhydrazino)carbonyl | CH2 | A2 | (2,3-dihydro-1,4-benzodioxin-2-ylcarbonyl)amino | H | H | H | | |
| 224 | phenyl | (2,2-dimethylhydrazino)carbonyl | CH2 | A16 | (tert-butoxycarbonyl)amino | H | | | | |
| 225 | phenyl | (2,2-dimethylhydrazino)carbonyl | CH2 | A16 | [(pentyloxy)carbonyl]amino | H | | | | |
| 226 | phenyl | (2,2-dimethylhydrazino)carbonyl | CH2 | A16 | [(but-3-yn-1-yloxy)carbonyl]amino | H | | | | |
| 227 | phenyl | (2,2-dimethylhydrazino)carbonyl | CH2 | A16 | [(pent-4-yn-2-yloxy)carbonyl]amino | H | | | | |
| 228 | phenyl | (2,2-dimethylhydrazino)carbonyl | CH2 | A16 | [(hex-5-yn-1-yloxy)carbonyl]amino | H | | | | |
| 229 | phenyl | (2,2-dimethylhydrazino)carbonyl | CH2 | A16 | benzoylamino | H | | | | |
| 230 | phenyl | (2,2-dimethylhydrazino)carbonyl | CH2 | A16 | (phenylacetyl)amino | H | | | | |
| 231 | phenyl | (2,2-dimethylhydrazino)carbonyl | CH2 | A16 | (phenoxyacetyl)amino | H | | | | |
| 232 | phenyl | (2,2-dimethylhydrazino)carbonyl | CH2 | A16 | [(2-phenylethoxy)carbonyl]amino | H | | | | |
| 233 | phenyl | (2,2-dimethylhydrazino)carbonyl | CH2 | A16 | [(cyclohexyloxy)acetyl]amino | H | | | | |
| 234 | phenyl | (2,2-dimethylhydrazino)carbonyl | CH2 | A16 | (3,4-dihydro-2H-chromen-2-ylcarbonyl)amino | H | | | | |
| 235 | phenyl | (2,2-dimethylhydrazino)carbonyl | CH2 | A16 | (2,3-dihydro-1,4-benzodioxin-2-ylcarbonyl)amino | H | | | | |
| 236 | phenyl | (trimethylhydrazino)carbonyl | CH2 | A2 | (tert-butoxycarbonyl)amino | H | H | H | | |
| 237 | phenyl | (trimethylhydrazino)carbonyl | CH2 | A2 | [(pentyloxy)carbonyl]amino | H | H | H | | |
| 238 | phenyl | (trimethylhydrazino)carbonyl | CH2 | A2 | [(but-3-yn-1-yloxy)carbonyl]amino | H | H | H | | |
| 239 | phenyl | (trimethylhydrazino)carbonyl | CH2 | A2 | [(pent-4-yn-2-yloxy)carbonyl]amino | H | H | H | | |

TABLE 1-continued

| Ex. | Q | T | L1 | An | Z1 | Z2 | Z3 | Z4 | logP | Mass (M + H) |
|---|---|---|---|---|---|---|---|---|---|---|
| 240 | phenyl | (trimethylhydrazino)carbonyl | CH2 | A2 | [(hex-5-yn-1-yloxy)carbonyl]amino | H | H | H | | |
| 241 | phenyl | (trimethylhydrazino)carbonyl | CH2 | A2 | benzoylamino | H | H | H | | |
| 242 | phenyl | (trimethylhydrazino)carbonyl | CH2 | A2 | (phenylacetyl)amino | H | H | H | | |
| 243 | phenyl | (trimethylhydrazino)carbonyl | CH2 | A2 | (phenoxyacetyl)amino | H | H | H | | |
| 244 | phenyl | (trimethylhydrazino)carbonyl | CH2 | A2 | [(2-phenylethoxy)carbonyl]amino | H | H | H | | |
| 245 | phenyl | (trimethylhydrazino)carbonyl | CH2 | A2 | [(cyclohexyloxy)acetyl]amino | H | H | H | | |
| 246 | phenyl | (trimethylhydrazino)carbonyl | CH2 | A2 | (3,4-dihydro-2H-chromen-2-ylcarbonyl)amino | H | H | H | | |
| 247 | phenyl | (trimethylhydrazino)carbonyl | CH2 | A2 | (2,3-dihydro-1,4-benzodioxin-2-ylcarbonyl)amino | H | H | H | | |
| 248 | phenyl | (trimethylhydrazino)carbonyl | CH2 | A2 | (tert-butoxycarbonyl)amino | H | H | H | | |
| 249 | phenyl | (trimethylhydrazino)carbonyl | CH2 | A2 | [(pentyloxy)carbonyl]amino | H | H | H | | |
| 250 | phenyl | (trimethylhydrazino)carbonyl | CH2 | A2 | [(but-3-yn-1-yloxy)carbonyl]amino | H | H | H | | |
| 251 | phenyl | (trimethylhydrazino)carbonyl | CH2 | A2 | [(pent-4-yn-2-yloxy)carbonyl]amino | H | H | H | | |
| 252 | phenyl | (trimethylhydrazino)carbonyl | CH2 | A2 | [(hex-5-yn-1-yloxy)carbonyl]amino | H | H | H | | |
| 253 | phenyl | (trimethylhydrazino)carbonyl | CH2 | A2 | benzoylamino | H | H | H | | |
| 254 | phenyl | (trimethylhydrazino)carbonyl | CH2 | A2 | (phenylacetyl)amino | H | H | H | | |
| 255 | phenyl | (trimethylhydrazino)carbonyl | CH2 | A2 | (phenoxyacetyl)amino | H | H | H | | |
| 256 | phenyl | (trimethylhydrazino)carbonyl | CH2 | A2 | [(2-phenylethoxy)carbonyl]amino | H | H | H | | |
| 257 | phenyl | (trimethylhydrazino)carbonyl | CH2 | A2 | [(cyclohexyloxy)acetyl]amino | H | H | H | | |
| 258 | phenyl | (trimethylhydrazino)carbonyl | CH2 | A2 | (3,4-dihydro-2H-chromen-2-ylcarbonyl)amino | H | H | H | | |
| 259 | phenyl | (trimethylhydrazino)carbonyl | CH2 | A2 | (2,3-dihydro-1,4-benzodioxin-2-ylcarbonyl)amino | H | H | H | | |
| 260 | phenyl | cyanocarbamoyl | CH2 | A2 | (tert-butoxycarbonyl)amino | H | H | H | | |
| 261 | phenyl | cyanocarbamoyl | CH2 | A2 | [(pentyloxy)carbonyl]amino | H | H | H | | |
| 262 | phenyl | cyanocarbamoyl | CH2 | A2 | [(but-3-yn-1-yloxy)carbonyl]amino | H | H | H | | |
| 263 | phenyl | cyanocarbamoyl | CH2 | A2 | [(pent-4-yn-2-yloxy)carbonyl]amino | H | H | H | | |
| 264 | phenyl | cyanocarbamoyl | CH2 | A2 | [(hex-5-yn-1-yloxy)carbonyl]amino | H | H | H | | |
| 265 | phenyl | cyanocarbamoyl | CH2 | A2 | benzoylamino | H | H | H | | |
| 266 | phenyl | cyanocarbamoyl | CH2 | A2 | (phenylacetyl)amino | H | H | H | | |
| 267 | phenyl | cyanocarbamoyl | CH2 | A2 | (phenoxyacetyl)amino | H | H | H | | |
| 268 | phenyl | cyanocarbamoyl | CH2 | A2 | [(2-phenylethoxy)carbonyl]amino | H | H | H | | |
| 269 | phenyl | cyanocarbamoyl | CH2 | A2 | [(cyclohexyloxy)acetyl]amino | H | H | H | | |
| 270 | phenyl | cyanocarbamoyl | CH2 | A2 | (3,4-dihydro-2H-chromen-2-ylcarbonyl)amino | H | H | H | | |
| 271 | phenyl | cyanocarbamoyl | CH2 | A2 | (2,3-dihydro-1,4-benzodioxin-2-ylcarbonyl)amino | H | H | H | | |
| 272 | phenyl | cyanocarbamoyl | CH2 | A2 | (tert-butoxycarbonyl)amino | H | H | H | | |
| 273 | phenyl | cyanocarbamoyl | CH2 | A2 | [(pentyloxy)carbonyl]amino | H | H | H | | |
| 274 | phenyl | cyanocarbamoyl | CH2 | A2 | [(but-3-yn-1-yloxy)carbonyl]amino | H | H | H | | |
| 275 | phenyl | cyanocarbamoyl | CH2 | A2 | [(pent-4-yn-2-yloxy)carbonyl]amino | H | H | H | | |
| 276 | phenyl | cyanocarbamoyl | CH2 | A2 | [(hex-5-yn-1-yloxy)carbonyl]amino | H | H | H | | |
| 277 | phenyl | cyanocarbamoyl | CH2 | A2 | benzoylamino | H | H | H | | |
| 278 | phenyl | cyanocarbamoyl | CH2 | A2 | (phenylacetyl)amino | H | H | H | | |
| 279 | phenyl | cyanocarbamoyl | CH2 | A2 | (phenoxyacetyl)amino | H | H | H | | |
| 280 | phenyl | cyanocarbamoyl | CH2 | A2 | [(2-phenylethoxy)carbonyl]amino | H | H | H | | |
| 281 | phenyl | cyanocarbamoyl | CH2 | A2 | [(cyclohexyloxy)acetyl]amino | H | H | H | | |
| 282 | phenyl | cyanocarbamoyl | CH2 | A2 | (3,4-dihydro-2H-chromen-2-ylcarbonyl)amino | H | H | H | | |
| 283 | phenyl | cyanocarbamoyl | CH2 | A2 | (2,3-dihydro-1,4-benzodioxin-2-ylcarbonyl)amino | H | H | H | | |
| 284 | phenyl | cyano(methyl)carbamoyl | CH2 | A2 | (tert-butoxycarbonyl)amino | H | H | H | | |
| 285 | phenyl | cyano(methyl)carbamoyl | CH2 | A2 | [(pentyloxy)carbonyl]amino | H | H | H | | |
| 286 | phenyl | cyano(methyl)carbamoyl | CH2 | A2 | [(but-3-yn-1-yloxy)carbonyl]amino | H | H | H | | |
| 287 | phenyl | cyano(methyl)carbamoyl | CH2 | A2 | [(pent-4-yn-2-yloxy)carbonyl]amino | H | H | H | | |
| 288 | phenyl | cyano(methyl)carbamoyl | CH2 | A2 | [(hex-5-yn-1-yloxy)carbonyl]amino | H | H | H | | |
| 289 | phenyl | cyano(methyl)carbamoyl | CH2 | A2 | benzoylamino | H | H | H | | |
| 290 | phenyl | cyano(methyl)carbamoyl | CH2 | A2 | (phenylacetyl)amino | H | H | H | | |
| 291 | phenyl | cyano(methyl)carbamoyl | CH2 | A2 | (phenoxyacetyl)amino | H | H | H | | |
| 292 | phenyl | cyano(methyl)carbamoyl | CH2 | A2 | [(2-phenylethoxy)carbonyl]amino | H | H | H | | |
| 293 | phenyl | cyano(methyl)carbamoyl | CH2 | A2 | [(cyclohexyloxy)acetyl]amino | H | H | H | | |
| 294 | phenyl | cyano(methyl)carbamoyl | CH2 | A2 | (3,4-dihydro-2H-chromen-2-ylcarbonyl)amino | H | H | H | | |
| 295 | phenyl | cyano(methyl)carbamoyl | CH2 | A2 | (2,3-dihydro-1,4-benzodioxin-2-ylcarbonyl)amino | H | H | H | | |
| 296 | phenyl | cyano(methyl)carbamoyl | CH2 | A2 | (tert-butoxycarbonyl)amino | H | H | H | | |
| 297 | phenyl | cyano(methyl)carbamoyl | CH2 | A2 | [(pentyloxy)carbonyl]amino | H | H | H | | |
| 298 | phenyl | cyano(methyl)carbamoyl | CH2 | A2 | [(but-3-yn-1-yloxy)carbonyl]amino | H | H | H | | |
| 299 | phenyl | cyano(methyl)carbamoyl | CH2 | A2 | [(pent-4-yn-2-yloxy)carbonyl]amino | H | H | H | | |
| 300 | phenyl | cyano(methyl)carbamoyl | CH2 | A2 | [(hex-5-yn-1-yloxy)carbonyl]amino | H | H | H | | |
| 301 | phenyl | cyano(methyl)carbamoyl | CH2 | A2 | benzoylamino | H | H | H | | |
| 302 | phenyl | cyano(methyl)carbamoyl | CH2 | A2 | (phenylacetyl)amino | H | H | H | | |
| 303 | phenyl | cyano(methyl)carbamoyl | CH2 | A2 | (phenoxyacetyl)amino | H | H | H | | |
| 304 | phenyl | cyano(methyl)carbamoyl | CH2 | A2 | [(2-phenylethoxy)carbonyl]amino | H | H | H | | |
| 305 | phenyl | cyano(methyl)carbamoyl | CH2 | A2 | [(cyclohexyloxy)acetyl]amino | H | H | H | | |

TABLE 1-continued

| Ex. | Q | T | L1 | An | Z1 | Z2 | Z3 | Z4 | logP | Mass (M + H) |
|---|---|---|---|---|---|---|---|---|---|---|
| 306 | phenyl | cyano(methyl)carbamoyl | CH2 | A2 | (3,4-dihydro-2H-chromen-2-ylcarbonyl)amino | H | H | H | | |
| 307 | phenyl | cyano(methyl)carbamoyl | CH2 | A2 | (2,3-dihydro-1,4-benzodioxin-2-ylcarbonyl)amino | H | H | H | | |
| 308 | phenyl | imino(1-methylhydrazino)methyl | CH2 | A2 | [(but-3-yn-1-yloxy)carbonyl]amino | H | H | H | 1.77 | 395 |
| 309 | phenyl | imino(methylsulfanyl)methyl | CH2 | A2 | [(but-3-yn-1-yloxy)carbonyl]amino | H | H | H | 3.02 | 397 |
| 310 | phenyl | carbamothioyl | CH2 | A2 | [(but-3-yn-1-yloxy)carbonyl]amino | H | H | H | 2.75 | 383 |

The following examples illustrate in a non-limiting manner the preparation and efficacy of the compounds of formula (I) according to the invention.

PREPARATION EXAMPLE 1 but-3-yn-1-yl{6-[({[cyano(phenyl)methylene]amino}oxy)methyl]pyridin-2-yl}carbamate (compound 3)

Step 1: Preparation of the Sodium Salt of α-(Hydroxyimino)(Phenyl)Acetonitrile

To a suspension of 3.3 g (83 mmol) of sodium hydroxyde in 50 ml of ethanol are added 9.7 g (83 mmol) of phenylacetonitrile. The reaction mixture is stirred until complete dissolution of the solid. While maintaining the temperature below 15° C., a solution of 11.7 g (100 mmol) of isopentyl nitrite in 10 ml of ethanol is then slowly added. The reaction mixture is further stirred at ambient temperature for 2 hrs. The reaction mixture is diluted by 100 ml of diethylether. The obtained solid is filtered, washed by diethylether and dried to yield 7.89 g (56% yield) of pure sodium salt of α-(hydroxyimino)(phenyl)-acetonitrile as a white solid. Melting point (mp): >200° C.

Step 2: preparation of but-3-yn-1-yl {6-[({[(Z)-cyano(phenyl)methylene]amino}oxy)methyl]-pyridin-2-yl}carbamate To a suspension of 1.05 g (6.25 mmol) of the sodium salt of α-(hydroxyimino)-(phenyl)acetonitrile in 25 ml of acetonitrile are successively added 104 mg (0.625 mmol) of potassium iodide and 1.49 g (6.25 mmol) of but-3-yn-1-yl [6-(chloromethyl)pyridin-2-yl]carbamate dissolved in 2.5 ml of N,N-dimethyl-formamide. The reaction mixture is stirred at ambient temperature for 16 hrs. The solvents are removed under vacuum and 100 ml of ethyl acetate are added. The organic layer is washed by brine, dried over magnesium sulfate and the residue obtained after concentration is crystallized upon diisopropylether to yield 2.21 g (99% yield) of one single isomer of but-3-yn-1-yl {6-[({[(Z)-cyano-(phenyl)methylene]amino}-oxy)methyl]pyridin-2-yl}carbamate as a white solid (M+H=349). mp: 76° C.

PREPARATION EXAMPLE 2 pentyl {6-[({[(2-(methylamino)-2-oxo-1-phenylethylidene]amino}oxy)-methyl]pyridin-2-yl}carbamate (compound 63)

Step 1: preparation of 2-{[(6-aminopyridin-2-yl)methoxy]imino}-N-methyl-2-phenylacetamide A homogeneous mixture of 461 mg (2.83 mmol) of N-methyl-2-oxo-2-phenylacetamide, 328 mg (2.36 mmol) of 6-[(aminooxy)methyl]pyridin-2-amine and 493 mg (2.6 mmol) of 4-toluenesulfonic acid monohydrate in 5 ml of isopropanol is heated at 160° C. for 1 hr in a microwave apparatus. The crude mixture is then cooled to ambient temperature and extracted by dichloromethane. The organic layer is washed by a solution of sodium carbonate, filtered over celite and concentrated. Column chromato-graphy (gradient dichloromethane/methanol) yielded 479 mg (71% yield) of a 68/32 Z/E mixture of 2-{[(6-aminopyridin-2-yl)methoxy]imino}-N-methyl-2-phenylacetamide as a yellow oil (M+H=285).

Step 2: preparation of pentyl {6-[({[(2-(methylamino)-2-oxo-1-phenylethylidene]amino}oxy)-methyl]-pyridin-2-yl}-carbamate To a mixture of 112 mg (0.71 mmol) of N-pentyl chloroformate and 60 mg (0.77 mmol) of pyridine in 5 ml of 1,4-dioxane, are added 168 mg of a 68/32 Z/E mixture of 2-{[(6-aminopyridin-2-yl)methoxy]imino}-N-methyl-2-phenylacetamide. The reaction mixture is stirred at ambient temperature for 16 hrs. The solvent is removed under vacuum and the crude is purified by column chromatography (gradient heptane/ethyl acetate) to yield 221 mg (93% yield) of a 69/31 Z/E mixture of pentyl {6-[({[(2-(methylamino)-2-oxo-1-phenylethylidene]amino}oxy)methyl]-pyridin-2-yl}-carbamate as an oil (M+H=399).

EXAMPLE A

Phytophthora Test (Tomato)/Preventive

Solvent: 49 parts by weight of N,N-dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of Phytophthora infestans. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control, while an efficacy of 100% means that no disease is observed. In this test the following compounds from table A according to the invention showed efficacy of 70% or even higher at a concentration of 500 ppm of active ingredient.

TABLE A

| Example | Efficacy |
|---|---|
| 75 | 85 |
| 98 | 85 |
| 99 | 95 |

TABLE A-continued

| Example | Efficacy |
|---|---|
| 100 | 70 |
| 101 | 95 |
| 109 | 98 |
| 110 | 70 |
| 111 | 92 |
| 112 | 100 |
| 129 | 92 |
| 130 | 100 |

The invention claimed is:

1. A compound of formula (I):

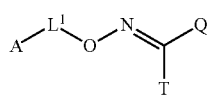

Wherein
T is selected in the list consisting of:
  a cyano group,
  a group of formula $T^a$

wherein
  X represents an oxygen atom, a sulfur atom, a $NR^a$ group; in which $R^a$ represents a hydrogen atom, a nitro group, a hydroxy group, a cyano group, an amino group, substituted or non-substituted $C_1$-$C_8$-alkyl, substituted or non-substituted $C_1$-$C_8$-cycloalkyl, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_2$-$C_8$-alkenyloxy, substituted or non-substituted $C_3$-$C_8$-alkynyloxy, substituted or non-substituted $C_1$-$C_8$-alkylsulfonyl, substituted or non-substituted arylsulfonyl, substituted or non-substituted benzyl, substituted or non-substituted benzyloxy, substituted or non-substituted benzylamino, substituted or non-substituted phenylamino, substituted or non-substituted aryl, or substituted or non-substituted heterocyclyl;
  W represents a hydrogen atom, a halogen atom, a hydroxy group, a cyano group, an amino group, a cyanoamino group, a sulfanyl group, hydrazino group, substituted or non-substituted N-($C_1$-$C_8$-alkyl)cyanoamino group, substituted or non-substituted $C_1$-$C_8$-alkoxyamino group, substituted or non-substituted N-($C_1$-$C_8$-alkyl)-($C_1$-$C_8$-alkoxy)-amino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-($C_1$-$C_8$)-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylsulfanyl, substituted or non-substituted $C_1$-$C_8$-alcylsulfinyl, substituted or non-substituted $C_1$-$C_8$-alkylsulfonyl, substituted or non-substituted $C_1$-$C_8$-halogenoalkylsulfanyl having 1 to 5 halogen atoms, substituted or non-substituted $C_1$-$C_8$-halogenoalkylsulfinyl having 1 to 5 halogen atoms, substituted or non-substituted $C_1$-$C_8$-halogenoalkylsulfonyl having 1 to 5 halogen atoms, substituted or non-substituted arylsulfanyl, substituted or non-substituted arylsulfinyl, substituted or non-substituted arylsulfonyl, substituted or non-substituted benzyloxy, substituted or non-substituted benzylsulfanyl, substituted or non-substituted benzylsulfinyl, substituted or non-substituted benzylsulfonyl, substituted or non-substituted benzylamino, substituted or non-substituted phenoxy, substituted or non-substituted phenylamino, substituted or non-substituted aryl, or substituted or non-substituted heterocyclyl;
a group of formula $T^b$

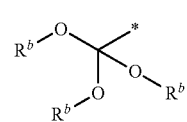

wherein
  $R^b$ independently represents a substituted or non-substituted $C_1$-$C_8$-alkyl;
a group of formula $T^c$

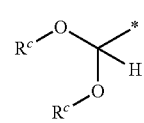

wherein
R$^c$ independently represents a substituted or non-substituted $C_1$-$C_8$-alkyl;
isonitrile group,
L$^1$ represents a direct bond or a divalent group consisting of —(CR$^1$R$^2$)$_n$—
wherein
n represents 1, 2, 3 or 4;
R$^1$ and R$^2$ independently represent a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, or substituted or non-substituted $C_3$-$C_8$-halogenoalkynyloxy having 1 to 5 halogen atoms,
A is selected in the list consisting of A$^2$, A$^{16}$, and A$^{18}$:

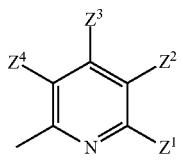
A$^2$

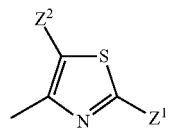
A$^{16}$

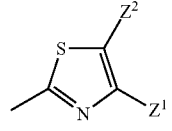
A$^{18}$ wherein
Z$^1$, Z$^2$, Z$^3$, and Z$^4$ independently represent a hydrogen atom, a halogen atom, a nitro group, a hydroxy group, a cyano group, an isonitrile group, an amino group, a cyanoamino group, a sulfanyl group, a formyl group, a substituted or non-substituted N-($C_1$-$C_8$-alkyl)cyanoamino group, a formyloxy group, a formylamino group, a carbamoyl group, a N-hydroxycarbamoyl group, a pentafluoro-$\lambda^6$-sulfanyl group, a formylamino group, substituted or non-substituted $C_1$-$C_8$-alkoxyamino group, substituted or non-substituted N-($C_1$-$C_8$-alkyl)-$C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, a substituted or non-substituted (hydroxyimino)-$C_1$-$C_6$-alkyl group, substituted or non-substituted $C_1$-$C_8$-alkyl, substituted or non-substituted tri-($C_1$-$C_8$-alkyl)silyl-$C_1$-$C_8$-alkyl, substituted or non-substituted $C_3$-$C_8$-cycloalkyl, substituted or non-substituted tri-($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted ($C_1$-$C_8$-alkoxycarbonyl)-amino, substituted or non-substituted ($C_3$-$C_8$-cycloalkoxycarbonyl)amino, substituted or non-substituted $C_1$-$C_8$-halogenoalkoxy having 1 to 5 halogen atoms, substituted or non-substituted $C_2$-$C_8$-alkenyloxy, substituted or non-substituted ($C_2$-$C_8$-alkenyloxycarbonyl)amino, substituted or non-substituted $C_2$-$C_8$-halogenoalkenyloxy having 1 to 5 halogen atoms, substituted or non-substituted $C_3$-$C_8$-alkynyloxy, substituted or non-substituted ($C_3$-$C_8$-alkynyloxycarbonyl)amino, substituted or non-substituted $C_3$-$C_8$-halogenoalkynyloxy having 1 to 5 halogen atoms, substituted or non-substituted $C_1$-$C_8$-alkylcarbonyl, substituted or non-substituted N-($C_1$-$C_8$-alkoxy)-$C_1$-$C_8$-alkanimidoyl, substituted or non-substituted N-($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-($C_1$-$C_8$-alkyl)carbamoyl, substituted or non-substituted N-($C_1$-$C_8$-alkyl)hydroxycarbamoyl, substituted or non-substituted $C_1$-$C_8$-alkoxycarbamoyl, substituted or non-substituted N-($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_3$-$C_7$-cycloalkylcarbonylamino, substituted or non-substituted $C_3$-$C_7$-halogenocycloalkylcarbonylamino having 1 to 5 halogen atoms, substituted or non-substituted aryloxycarbonylamino, substituted or non-substituted heterocyclyloxycarbonylamino, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-($C_1$-$C_8$-alkyl)carbamoylamino, substituted or non-substituted di-($C_1$-$C_8$-halogenoalkyl)carbamoylamino having 1 to 5 halogen atoms, substituted or non-substituted N-($C_1$-$C_8$-alkyl)-($C_1$-$C_8$-alkylcarbamoyl)amino, substituted or non-substituted N-($C_1$-$C_8$-alkyl)-($C_1$-$C_8$-halogenoalkylcarbamoy)amino having 1 to 5 halogen atoms, substituted or non-substituted N-($C_1$-$C_8$-alkyl)-(di-$C_1$-$C_8$-alkylcarbamoyl)amino, substituted or non-substituted N-($C_1$-$C_8$-alkyl)-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di -($C_1$-$C_r$alkyl)aminocarbonyloxy, substituted or non-substituted $C_1$-$C_8$-alkylearbamothioyl, substituted or non-substituted di-($C_1$-$C_8$-alkyl)carbamothioyl, substituted or non-substituted N -($C_1$-$C_8$-alkyl)hydroxyearbamothioyl, substituted or non-substituted $C_1$-$C_8$ alkoxycarbamothioyl, substituted or non-substituted N-($C_1$-$C_8$-alkyl)-$C_1$-$C_8$-alkoxyearbamothioyl, substituted or non-substituted $C_1$-$C_8$-alkylthioylamino, substituted or non-substituted ($C_1$-$C_8$-alkoxythiocarbonyl)amino, substituted or non-substituted $C_1$-$C_8$-halogenoalkylthioylamino having 1 to 5 halogen atoms, substituted or non-substituted $C_1$-$C_8$-alkyl-carbamothioyloxyl, substituted or non-substituted substituted or non-substituted di-($C_1$-$C_8$-alkyl)-carbamothioyloxy, substituted or non-substituted $C_1$-$C_g$-alkylsulfanyl, substituted or non-substituted $C_1$-$C_8$-halogenoalkylsulfanyl having 1 to 5 halogen atoms, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkysulfamoyl, substituted or non-substituted di-($C_1$-$C_8$-alkyl) sulfamoyl, substituted or non-substituted ($C_1$-$C_8$-alkoxyimino)-$C_1$-$C_8$-alkyl, substituted or non-substituted ($C_2$-$C_8$-alkenyloxyimino)-$C_1$-$C_8$-alkyl, substituted or non-substituted ($C_2$-$C_8$-alleynyloxyimMo)-$C_1$-$C_8$-alkyl, substituted or non-substituted (benzyloxyimino)-$C_1$-$C_8$-alkyl, substituted or non-substituted benzyloxy, substituted or non-substituted benzylsulfanyl, substituted or non-substituted benzylamino, substituted or non-substituted phenoxy, substituted or non-substituted phenylsulfanyl, substituted or non-substituted phenylamino, substituted or non-substituted aryl, substituted or non-substituted arylcarbonylamino, substituted or non-substituted heterocyclylcarbonylamino, substituted or non-substituted aryl-$C_1$-$C_8$-alkyl, substituted or non-substituted tri-($C_1$-$C_8$-alkyl)-silyloxy, substituted or non-substituted $C_1$-$C_8$-alkylsulfanylamino, substituted or non-substituted $C_1$-$C_8$-halogenoalkylsulfanylamino having 1 to 5 halogen atoms, substituted or non-substituted $C_1$-$C_8$-alkylsulfinylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri-($C_1$-$C_8$-alkyl)-silyl, substituted or non-substituted ($C_1$-$C_8$-alkylideneamino)oxy, substituted or non-substituted ($C_3$-$C_8$-alkenylideneamino)oxy, substituted or non-substituted ($C_3$-$C_8$-alkynylideneamino)oxy, substituted or non-substituted (benzylideneamino)oxy, substituted or non-substituted aryl-cyclopropylcarbonylamino, substituted or non-substituted $C_3$-$C_8$-cycloalkenylcarbonylamino, substituted or non-substituted $C_2$-$C_8$-alkenylcarbonylamino, substituted or non-substituted $C_2$-$C_8$-alkynylcarbonylamino, substituted or non-substituted $C_8$-$C_{12}$-fused bicycloalkylcarbonylamino, or substituted or non-substituted $C_5$-$C_{12}$-fused bicycloalkenylcarbonylamino;

Q is selected in the list consisting of $Q^1$ :

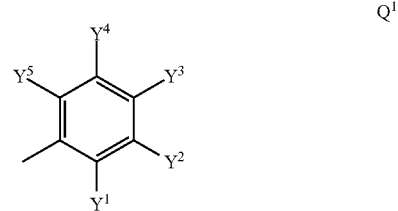

wherein $Y^1$ to $Y^5$ independently represent a hydrogen atom, a nitro group, a hydroxy group, a cyano group, an isonitrile group, an amino group, a sulfanyl group, a formyl group, a formyloxy group, a formylamino group, a carbamoyl group, a N-hydroxycarbamoyl group, a pentafluoro-$\lambda^6$-sulfanyl group, a formylamino group, substituted or non-substituted $C_1$-$C_8$-alkoxyamino group, substituted or non-substituted N-($C_1$-$C_8$-alkyl)-$C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri-($C_1$-$C_8$-alkyl)hydrazino group, substituted or non-substituted (hydroxyimino)-$C_1$-$C_6$-alkyl group, substituted or non-substituted $C_1$-$C_8$-alkyl, substituted or non-substituted tri-($C_1$-$C_8$-alkyl)silyl-$C_1$-$C_8$-alkyl, substituted or non-substituted $C_3$-$C_7$-cycloalkyl, substituted or non-substituted tri-($C_1$-$C_8$-alkyl)silyl-$C_3$-$C_7$-cycloalkyl, substituted or non-substituted $C_1$-$C_8$-halogenoalkyl having 1 to 5 halogen atoms, substituted or non-substituted $C_3$-$C_7$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di -($C_1$-$C_8$-alkyl)amino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N-($C_1$-$C_8$-alkoxy)-$C_1$-$C_8$-alkanimidoyl, substituted or non-substituted N-($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-($C_1$-$C_8$-alkyl)carbamoyl, substituted or non-substituted N-($C_1$-$C_8$-alkyl)hydroxycarbamoyl, substituted or non-substituted $C_1$-$C_8$-alkoxycarbamoyl, substituted or non-substituted N-($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-($C_1$-$C_8$-alkyl)carbamoylamino, substituted or non-substituted di-($C_1$-$C_8$-halogenoalkyl)carbamoylamino having 1 to 5 halogen atoms, substituted or non-substituted N -($C_1$-$C_8$-alkyl)-($C_1$-$C_8$-alkylcarbamoyl)amino, substituted or non-substituted N-($C_1$-$C_8$-alkyl) -($C_1$-$C_8$-halogenoalkylcarbamoyl)amino having 1 to 5 halogen atoms, substituted or non-substituted N-($C_1$-$C_8$-alkyl)-[di-($C_1$-$C_8$-alkyl)carbamoyl]amino, substituted or non-substituted N -($C_1$-$C_8$-alkyl)-[di-($C_1$-$C_8$-halogenoalkyl)carbamoyl]amino having 1 to 5 halogen atoms, substituted or non-substituted $C_1$-$C_8$-alkylaminocarbonyloxy, substituted or non-substituted di -($C_1$-$C_z$alkylamino)carbonyloxy, substituted or non-substituted $C_1$-$C_8$-alkylcarbamothioyl, substituted or non-substituted di-($C_1$-$C_8$-alkyl)carbamothioyl, substituted or non-substituted N -($C_1$-$C_8$-alkyl)hydroxycarbamothioyl, substituted or non-substituted $C_1$-$C_8$-alkoxycarbamothioyl, substituted or non-substituted N-($C_1$-$C_8$-alkyl)-$C_1$-$C_8$-alkoxycarbamothioyl, substituted or non-substituted $C_1$-$C_8$ -alkylthioylamino, substituted or non-substituted $C_1$-$C_8$-halogenoalkylthioylamino having 1 to 5 halogen atoms, substituted or non-substituted $C_1$-$C_8$-alkyl-carbamothioyloxy, substituted or non-substituted substituted or non-substituted di-($C_1$-$C_8$-alkyl)-carbamothioyloxy, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkysulfamoyl, substituted or non-substituted di-($C_1$-$C_8$-alkyl)sulfamoyl, substituted or non-substituted ($C_1$-$C_8$-alkoxyimino)-$C_1$-$C_8$-alkyl, substituted or non-substituted ($C_2$-$C_8$-alkenyloxyimino)-$C_1$-$C_8$-alkyl, substituted or non-substituted ($C_3$-$C_8$-alkynyloxyimino) -$C_1$-$C_8$-alkyl, substituted or non-substituted (benzyloxyimino)-$C_1$-$C_8$-alkyl, substituted or non-substituted benzyloxy, substituted or non-substituted benzylsulfanyl, substituted or non-substituted benzylamino, substituted or non-substituted phenoxy, substituted or non-substituted phenylsulfanyl, substituted or non-substituted phenylamino, substituted or non-substituted aryl, substituted or non-substituted aryl-$C_1$-$C_8$-alkyl, substituted or non-substituted tri-($C_1$-$C_8$-alkyl) -silyloxy, substituted or non-substituted $C_1$-$C_8$-alkylsulfanylamino, substituted or non-substituted $C_1$-$C_8$-halogenoalkylsulfanylamino having 1 to 5 halogen atoms, substituted or non-substituted $C_1$-$C_8$-alkylsulfinylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri-($C_1$-$C_8$-alkyl)-silyl, substituted or non-substituted ($C_1$-$C_8$-alkylideneamino)oxy, substituted or non-substituted ($C_1$-$C_8$-alkenylideneamino)oxy, substituted or non-substituted ($C_1$-$C_8$-alkynylideneamino)oxy, or substituted or non-substituted (benzylideneamino)oxy;

provided that when A is $A^2$ and T is a cyano group, $Z^1$ is not hydrogen;

as well as salts, N-oxides, metallic complexes and metalloidic complexes thereof or (E) and (Z) isomers and mixtures thereof.

2. A compound according to claim 1 wherein T represents a cyano group or a group of formula $T^a$.

3. A compound according to claim 1 wherein X represents an oxygen atom.

4. A compound according to claim 1 wherein $R^a$ represents a hydrogen atom, a hydroxy group, substituted or non-substituted $C_1$-$C_8$-alkyl, substituted or non-substituted $C_3$-$C_7$-cycloalkyl.

5. A compound according to claim 1 wherein $R^a$ independently represents a hydrogen atom, a methyl group or an ethyl group.

6. A compound according to claim 1 wherein W represents a hydrogen atom, a halogen atom, a hydroxy group, a cyano group, an amino group, a cyanoamino group, a sulfanyl group, a hydrazino group, a substituted or non-substituted N-($C_1$-$C_8$-alkyl)cyanoamino group, substituted or non-substituted $C_1$-$C_8$-alkoxyamino group, substituted or non-substituted N-($C_1$-$C_8$-alkyl)-$C_1$-$C_8$-alkoxyamino group, substituted or non-substituted 1-($C_1$-$C_8$-alkyl)hydrazino group, substituted or non-substituted 2-($C_1$-$C_8$-alkyl)hydrazino group, substituted or non-substituted 1,2-di-($C_1$-$C_8$-alkyl)hydrazino group, substituted or non-substituted 2,2-di-($C_1$-$C_8$-alkyl)hydrazino group, substituted or non-substituted tri -($C_1$-$C_8$-alkyl)hydrazino group, substituted or non-substituted $C_1$-$C_8$-alkyl, substituted or non-substituted $C_1$-$C_7$-cycloalkyl, substituted or non-substituted $C_1$-$C_8$-halogenoalkyl having 1 to 5 halogen atoms, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_1$-$C_8$-alkylsulfanyl.

7. A compound according to claim 6 wherein W represents a hydroxy group, an amino group, a hydrazino group, substituted or non-substituted $C_1$-$C_8$-alkoxyamino group, substituted or non-substituted N-($C_1$-$C_8$-alkyl)-$C_1$-$C_8$-alkoxyamino group, substituted or non-substituted $C_1$-$C_8$-alkylamino, substituted or non-substituted di-($C_1$-$C_8$-alkyl)amino, substituted or non-substituted $C_1$-$C_8$-alkoxy, substituted or non-substituted $C_1$-$C_8$-alkylsulfanyl.

8. A compound according to claim 6 wherein W represents a hydroxy group, an amino group, a hydrazino group, methylamino, ethylamino, dimethylamino, ethylmethylamino or methoxy.

9. A compound according to claim 1 wherein $R^b$ represents methyl or ethyl.

10. A compound according to claim 1 wherein $R^c$ represents methyl or ethyl.

11. A compound according to claim 1 wherein $L^1$ represents a direct bond or a divalent group consisting of —$(CR^1R^2)$— wherein
n represents 1 or 2 ;
$R^1$ and $R^2$ independently represent a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms.

12. A compound according to claim 1 wherein $L^1$ represents a direct bond or a divalent group consisting of —$(CR^1 R^2)$—, wherein $R^1$ and $R^2$ are independently selected in the list consisting of hydrogen, halogen, methyl, ethyl, isopropyl, trifluoromethyl, difluoromethyl, allyl, ethynyl, propargyl, cyclopropyl, methoxy, trifluoromethoxy and cyano.

13. A compound according to claim 1 wherein $Z^1$ represents independently represent a hydrogen atom, a halogen atom, a nitro group, a hydroxy group, a cyano group, an amino group, a formylamino group, substituted or non-substituted $C_1$-$C_8$-alkyl, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted ($C_1$-$C_8$-alkoxycarbonyl)amino, substituted or non-substituted ($C_3$-$C_8$-cycloalkoxycarbonyl)amino, substituted or non-substituted ($C_2$-$C_8$-alkenyloxycarbonyl)amino, substituted or non-substituted ($C_3$-$C_8$-alkynyloxycarbonyl)amino, substituted or non-substituted $C_1$-$C_8$-alkylcarbamoyl, substituted or non-substituted di-($C_1$-$C_8$-alkyl)carbamoyl, substituted or non-substituted N-($C_1$-$C_8$-alkyl)hydroxycarbamoyl, substituted or non-substituted $C_1$-$C_8$-alkoxycarbamoyl, substituted or non-substituted N-($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-alkylcarbonylamino, substituted or non-substituted aryloxycarbonylamino, substituted or non-substituted heterocyclyloxycarbonylamino, substituted or non-substituted $C_1$-$C_8$-alkylcarbamoylamino, substituted or non-substituted $C_1$-$C_8$-alkylthioylamino, substituted or non-substituted ($C_1$-$C_8$-alkoxythiocarbonyl)amino, substituted or non-substituted (arylcarbonyl)amino, substituted or non-substituted (heterocyclylcarbonyl)-amino, substituted or non-substituted arylcyclopropylcarbonylamino, substituted or non-substituted $C_3$-$C_7$-cycloalkenylcarbonylamino, substituted or non-substituted $C_2$-$C_8$-alkenylcarbonylamino, substituted or non-substituted $C_2$-$C_8$-alkynylcarbonylamino, substituted or non-substituted $C_5$-$C_{12}$-fused bicycloalkylcarbonylamino, substituted or non-substituted $C_5$-$C_{12}$-fused bicycloalkenylcarbonylamino.

14. A compound according to claim 1 wherein $Z^1$ represents an amino group, a formylamino group, substituted or non-substituted ($C_1$-$C_8$-alkoxycarbonyl)amino, substituted or non-substituted ($C_2$-$C_8$-alkenyloxycarbonypamino, substituted or non-substituted ($C_3$-$C_8$-alkynyloxycarbonyl) amino, substituted or non-substituted $C_1$-$C_8$-alkylthioylamino, substituted or non-substituted (arylcarbonyl)amino, substituted or non-substituted (heterocyclylcarbonyl)amino, substituted or non-substituted aryl-cyclopropylcarbonylamino, substituted or non-substituted $C_3$-$C_7$-cycloalkenylcarbonylamino, substituted or non-substituted $C_2$-$C_8$-alkenylcarbonylamino, substituted or non-substituted $C_2$-$C_8$-alkynylcarbonylamino.

15. A compound according to claim 1 wherein $Z^1$ represents an amino group, a formylamino group, substituted or non-substituted ($C_4$-$C_8$-alkoxycarbonyl)amino, substituted or non-substituted ($C_4$-$C_8$-alkenyloxycarbonyl)amino, substituted or non-substituted ($C_4$-$C_8$-alkynyloxycarbonyl) amino, substituted or non-substituted $C_4$-$C_8$-alkylthioylamino, substituted or non-substituted (arylcarbonyl)amino, substituted or non-substituted (heterocyclylcarbonyl)amino.

16. A compound according to claim 1 wherein $Z^2$ to $Z^4$ independently represent a hydrogen atom, a halogen atom, a cyano group, substituted or non-substituted $C_1$-$C_8$-alkyl, substituted or non-substituted $C_3$-$C_7$-cycloalkyl, substituted or non-substituted $C_1$-$C_8$-halogenoalkyl having 1 to 5halogen atoms, substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted phenoxy, substituted or non-substituted aryl, substituted or non-substituted aryl-$C_1$-$C_8$-alkyl.

17. A compound according to claim 1 wherein $Z^2$ to $Z^4$ are independently selected in the list consisting of hydrogen, halogen, methyl, ethyl, isopropyl, isobutyl, terbutyl, trifluoromethyl, difluoromethyl, allyl, ethynyl, propargyl, cyclopropyl, methoxy, trifluoromethoxy, acetyl, and cyano.

18. A compound according to any one of claim 1 wherein $Y^1$ to $Y^5$ independently represent a hydrogen atom, a halogen atom, a cyano group, an amino group, a sulfanyl group, a pentafluoro$\lambda^6$-sulfanyl group, substituted or non-substituted $C_1$-$C_8$-alkyl, substituted or non-substituted tri-($C_1$-$C_8$-alkyl) silyl-$C_1$-$C_8$-alkyl, substituted or non-substituted $C_3$-$C_7$-cycloalkyl, substituted or non-substituted tri-($C_1$-$C_8$-alkyl)silyl-$C_3$-$C_7$-cycloalkyl, substituted or non-substituted $C_1$-$C_8$halogenoalkyl having 1 to 5 halogen atoms, substituted or non-substituted $C_1$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$ alkoxy, substituted or non-substituted $C_1$-$C_8$-halogenoalkoxy having 1 to 5 halogen atoms, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N-($C_1$-$C_8$-alkoxy)-$C_1$-$C_8$-alkanimidoyl, substituted or non-substituted N -($C_1$-$C_8$-alkoxy)-$C_1$-$C_8$-halogenoallcanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-($C_1$-$C_8$-alkyl) carbamoyl, substituted or non-substituted N-($C_1$-$C_8$-alkyl) hydroxycarbamoyl, substituted or non-substituted $C_1$-$C_8$- alkoxycarbamoyl, substituted or non-substituted N-($C_1$-$C_8$-alkyl)-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-($C_1$-$C_8$-alkyl)carbamothioyl, substituted or non-substituted N-($C_1$-$C_8$-alkyphydroxycarbamothioyll, substituted or non-substituted $C_1$-$C_8$-alkoxycarbamothioyl, substituted or non-substituted N-($C_1$-$C_8$-alkyl)-$C_1$-$C_8$-alkoxycarbamothioyl, substituted or non-substituted $C_1$-$C_8$-alkylsulfanyl, substituted or non-substituted $C_1$-$C_8$-halogenoalkylsulfanyl having 1 to 5 halogen atoms, substituted or non-substituted $C_1$-$C_8$-alkyl-sulfonyl, substituted or non-substituted $C_1$-$C_8$-halogenoalkylsulfonyl having 1 to 5 halogen atoms, substituted or non-substituted ($C_1$-$C_8$-alkoxyimino)-$C_1$-$C_8$-alkyl, substituted or non-substituted ($C_2$-$C_8$-alkenyloxyimino)-$C_1$-$C_8$-alkyl, substituted or non-substituted ($C_3$-$C_8$-alkynyloxyimino)-$C_1$-$C_8$-alkyl, substituted or non-substituted (benzyloxyimino)-$C_1$-$C_8$-alkyl, substituted or non-substituted benzyloxy, substituted or non-substituted benzylsulfanyl, substituted or non-substituted phenoxy, substituted or non-substituted phenylsulfanyl, substituted or non-substituted aryl, substituted or non-substituted aryl-$C_1$-$C_8$-alkyl, substituted or non-substituted tri-($C_1$-$C_8$-alkyl)-silyloxy, substituted or non-substituted tri-($C_1$-$C_8$-alkyl)-silyl.

19. A compound according to claim 1 wherein $Y^1$ to $Y^5$ independently represent a hydrogen atom, a halogen atom, methyl, isopropyl, isobutyl, tertbutyl, trifluoromethyl, difluoromethyl, allyl, ethynyl, propargyl, cyclopropyl, methoxy, trifluoromethoxy and cyano.

20. A fungicide composition comprising, as an active ingredient, an effective amount of a compound of formula (I) according to claim 1 and an agriculturally acceptable support, carrier or filler.

21. A method for controlling phytopathogenic fungi of plants, crops or seeds, comprising applying an agronomically effective and substantially non-phytotoxic quantity of a compound according to claim 1 to the soil where plants grow or are capable of growing, to the leaves and/or the fruit of plants or to the seeds of plants.

22. A method for controlling phytopathogenic fungi of plants, crops or seeds, comprising applying an agronomically effective and substantially non-phytotoxic quantity of a fungicide composition according to claim 20 to the soil where plants grow or are capable of growing, to the leaves and/or the fruit of plants or to the seeds of plants.

* * * * *